US005565621A

United States Patent [19]
Selby et al.

[11] Patent Number: 5,565,621
[45] Date of Patent: Oct. 15, 1996

[54] STACKED COMPONENT TAPERED BEARING SIMULATOR DEVICE

[75] Inventors: Theodore W. Selby; Gregory C. Miiller, both of Midland, Mich.

[73] Assignee: Tannas Co., Midland, Mich.

[21] Appl. No.: 543,657

[22] Filed: Oct. 16, 1995

[51] Int. Cl.$^6$ ............................ G01N 11/16; G01N 11/14; G01M 19/00
[52] U.S. Cl. ...................... 73/54.28; 73/54.35; 73/862.08
[58] Field of Search ............................. 73/54.28, 54.32, 73/54.35, 54.23, 862.08, 862.54

[56] References Cited

U.S. PATENT DOCUMENTS

| | | | |
|---|---|---|---|
| 2,846,873 | 8/1958 | Källe | 73/59 |
| 2,957,339 | 10/1960 | Penny et al. | 73/59 |
| 3,111,838 | 11/1963 | Bucalo | 73/54 |
| 3,128,620 | 4/1964 | Gupta | 73/60 |
| 3,292,423 | 12/1966 | Banks | 73/60 |
| 3,350,922 | 11/1967 | Kim et al. | 73/60 |
| 3,886,789 | 6/1975 | Brookfield | 73/59 |
| 4,334,424 | 6/1982 | Kepes | 73/59 |
| 4,445,365 | 5/1984 | Selby | 73/60 |
| 4,596,154 | 6/1986 | Greubel | 73/862.08 |
| 4,633,702 | 1/1987 | Kaiser et al. | 73/9 |
| 5,301,541 | 4/1994 | Joseph et al. | 73/54.32 |
| 5,369,988 | 12/1994 | Selby | 73/54.28 |

OTHER PUBLICATIONS

ASTM D 4683–90.
Hydrick, *Lubricants World*, Dec. 1994, pp. 7, 10–11 & 14.
Tannas Co., Catalog, Midland, Mich., 1994, pp. 2 & 3.

*Primary Examiner*—Hezron E. Williams
*Assistant Examiner*—J. David Wiggins
*Attorney, Agent, or Firm*—Christopher John Rudy; William Miller Yates

[57] ABSTRACT

Exemplary stacked component tapered bearing simulator device, the principles of which can be applied more broadly in such instrumentation as dynamometers and viscometers, can have a stator block with a sample receiving bore; a rotor complementary to the stator block bore extending axially into the bore to define a thin measuring gap, the rotor having a drive shaft extending axially upward from it; a motor, which can rotate in response to torque from a test sample present in the thin gap and which drives the shaft and rotor along a rotation axis; a part for sensing the torque, fixable to the motor, and connectable to a platform that is vertically adjustable by an elevator mechanism, which generally, externally bounds the axis of rotation of the motor, drive shaft, and rotor. Preferably, the elevator mechanism has a threaded arrangement with an anti-rotation device with a first set of threads residing with the platform, which is restrained from rotating by the anti-rotation device but is allowed to move vertically, and a second set of threads for mating with the first set of threads residing with at least one rotatable member separate from but threadedly engagable with the set of platform threads.

20 Claims, 20 Drawing Sheets

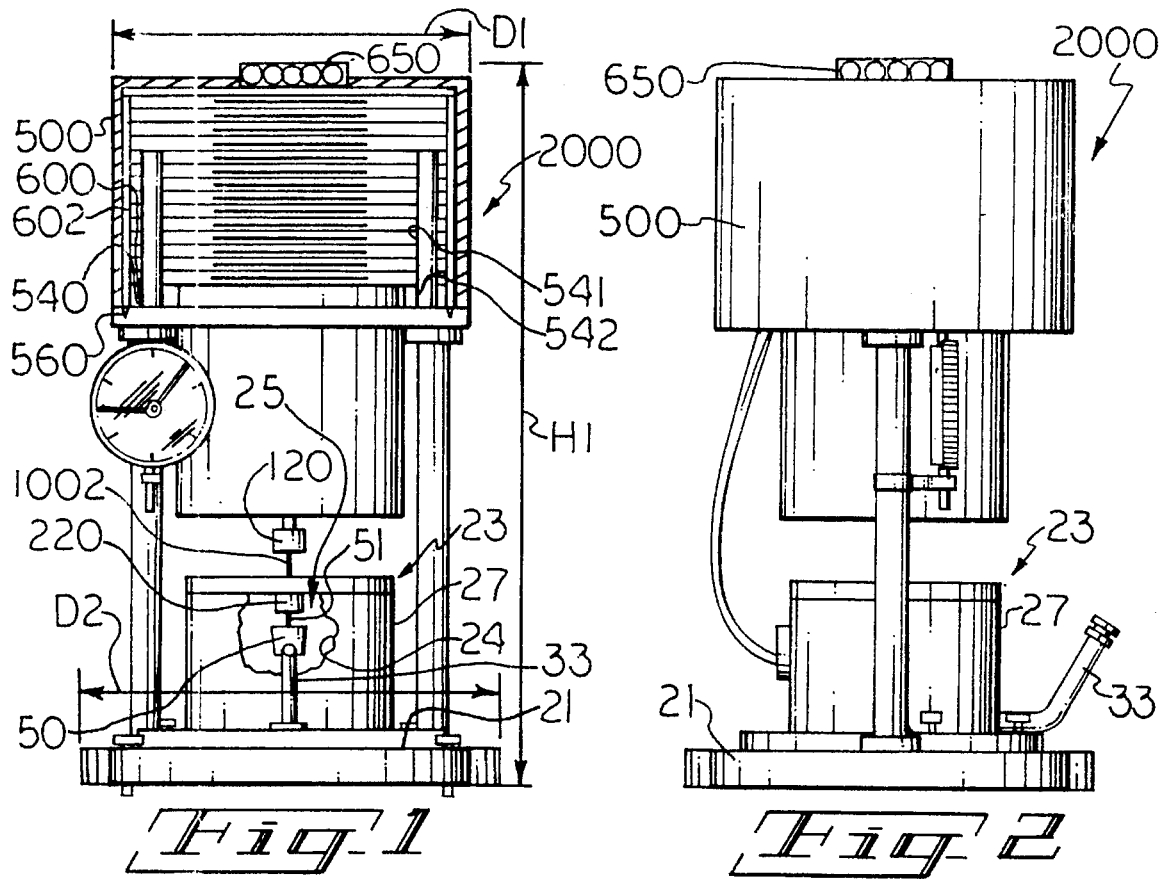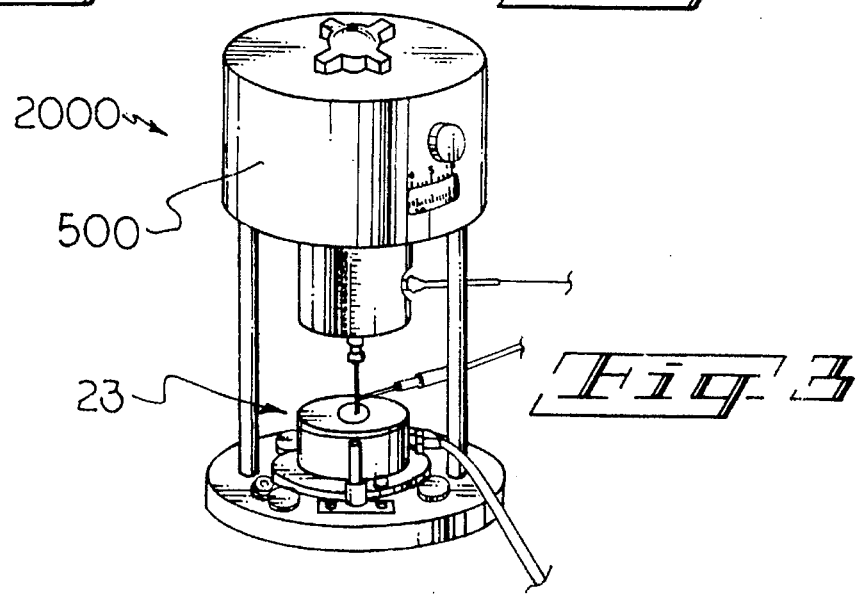

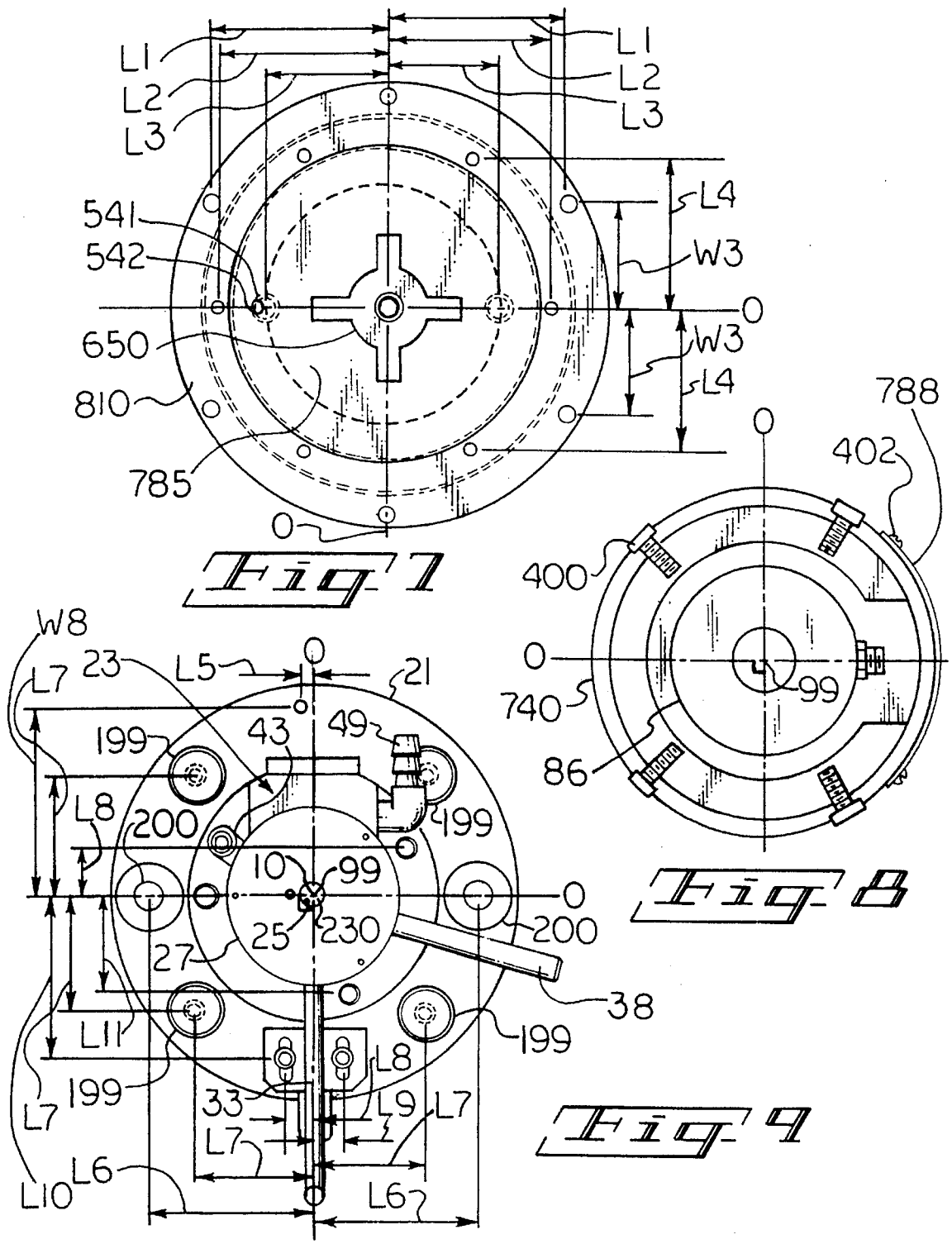

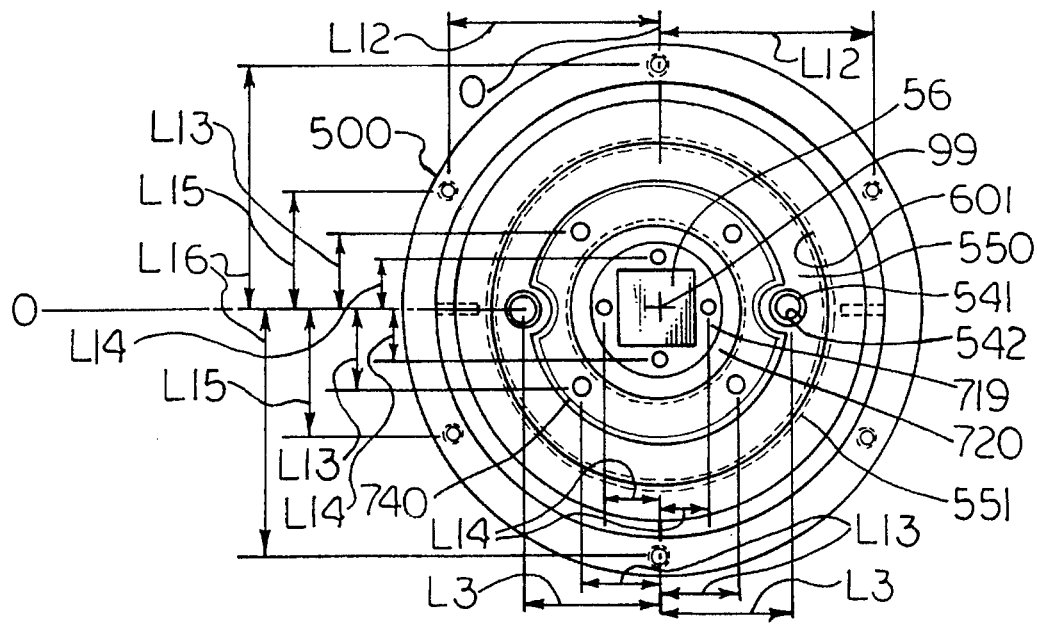
Fig 10
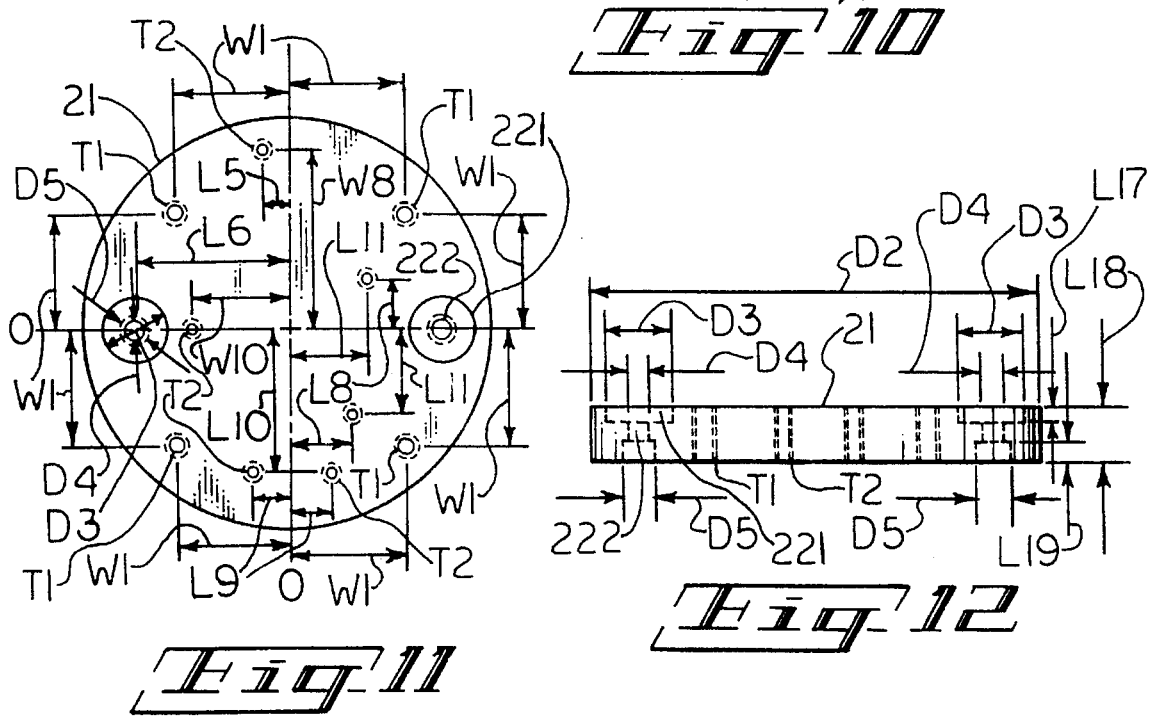
Fig 11
Fig 12

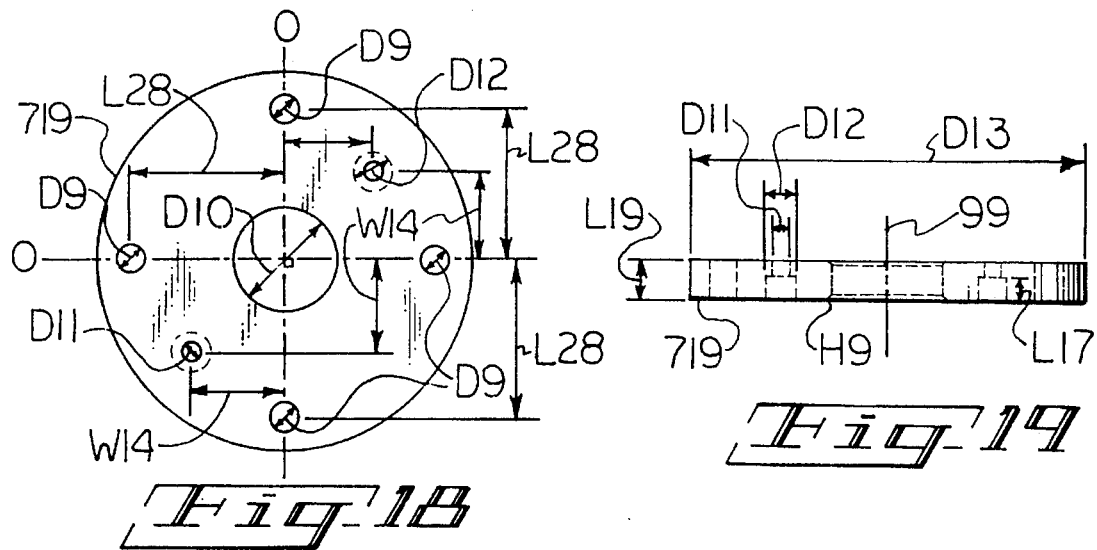
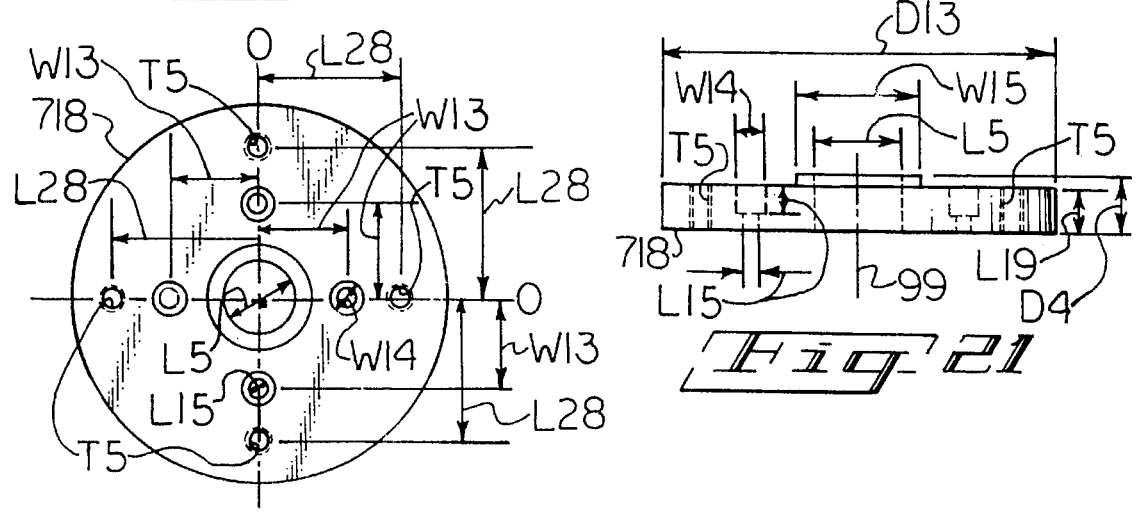
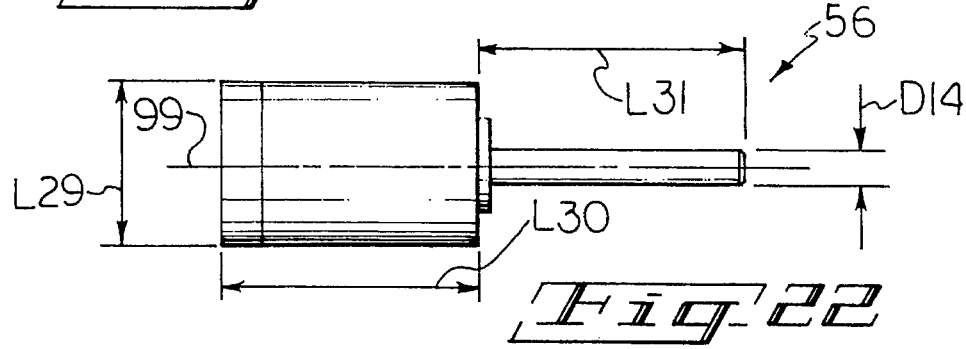

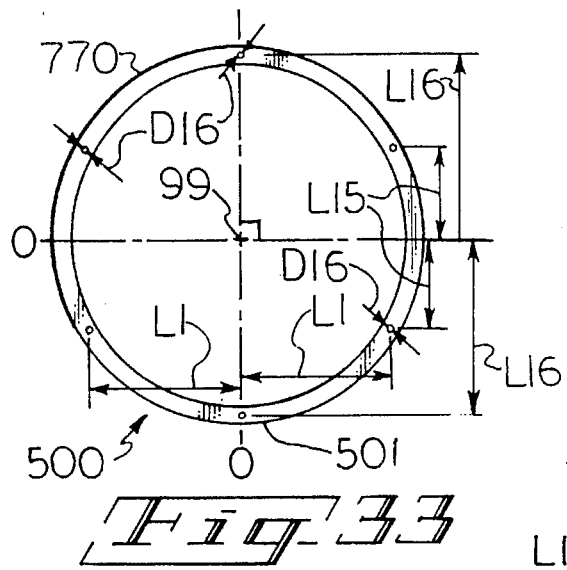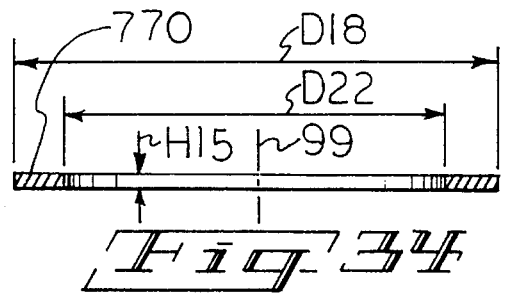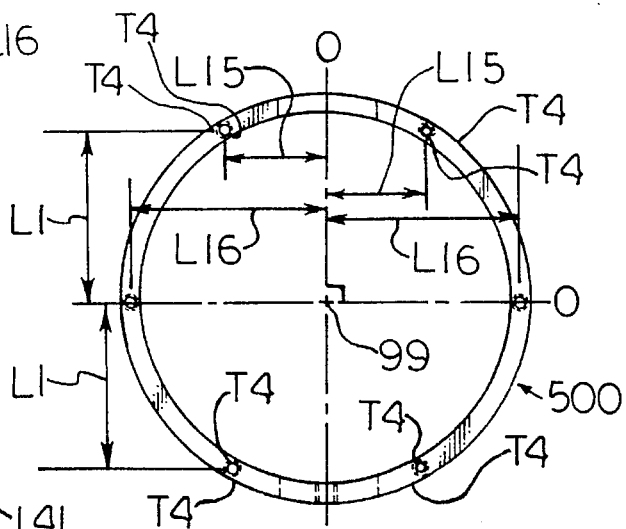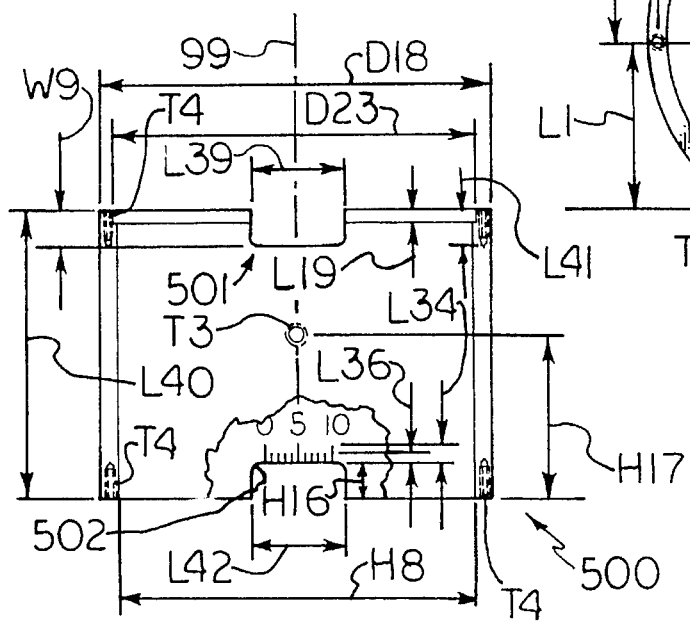

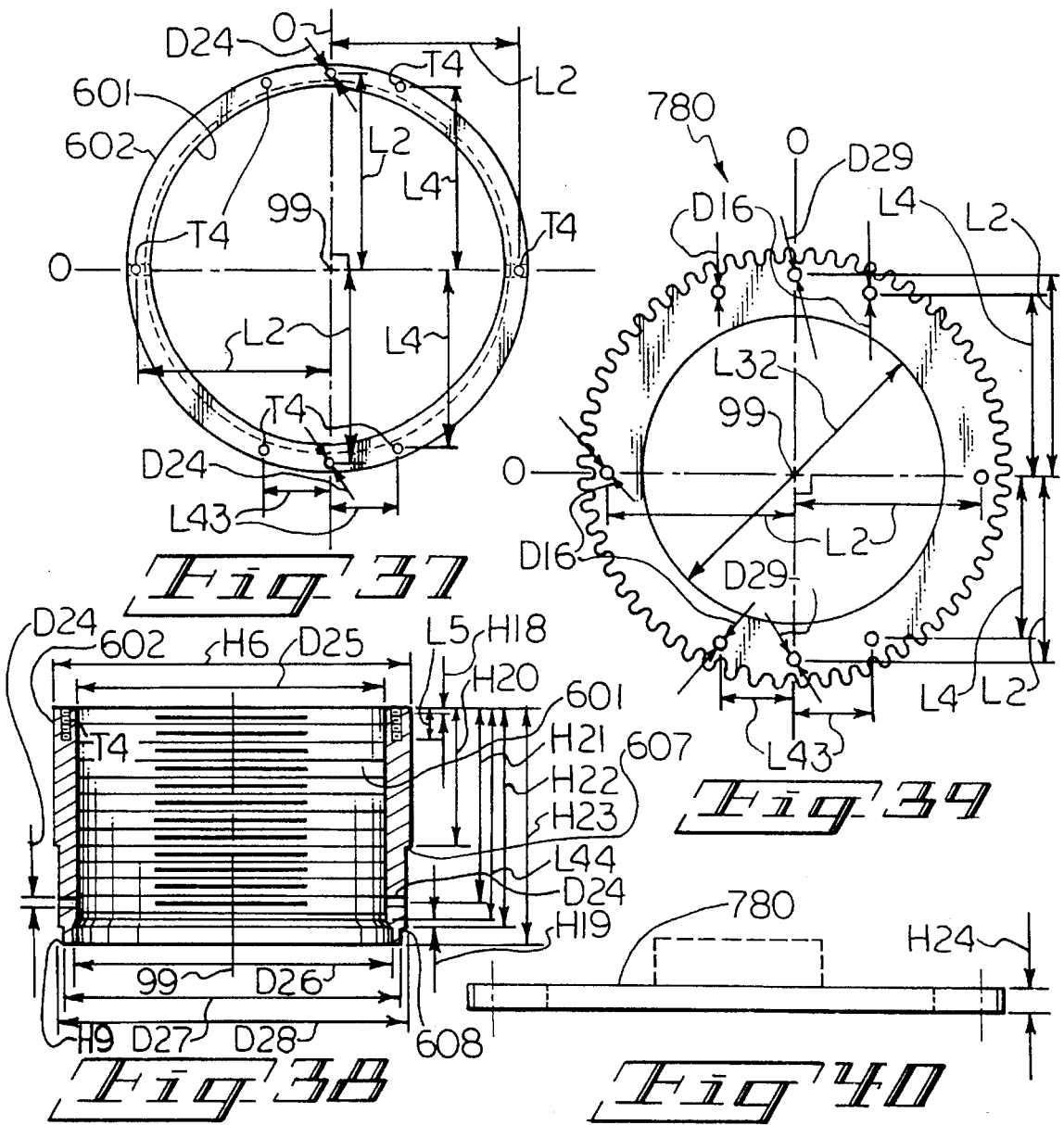

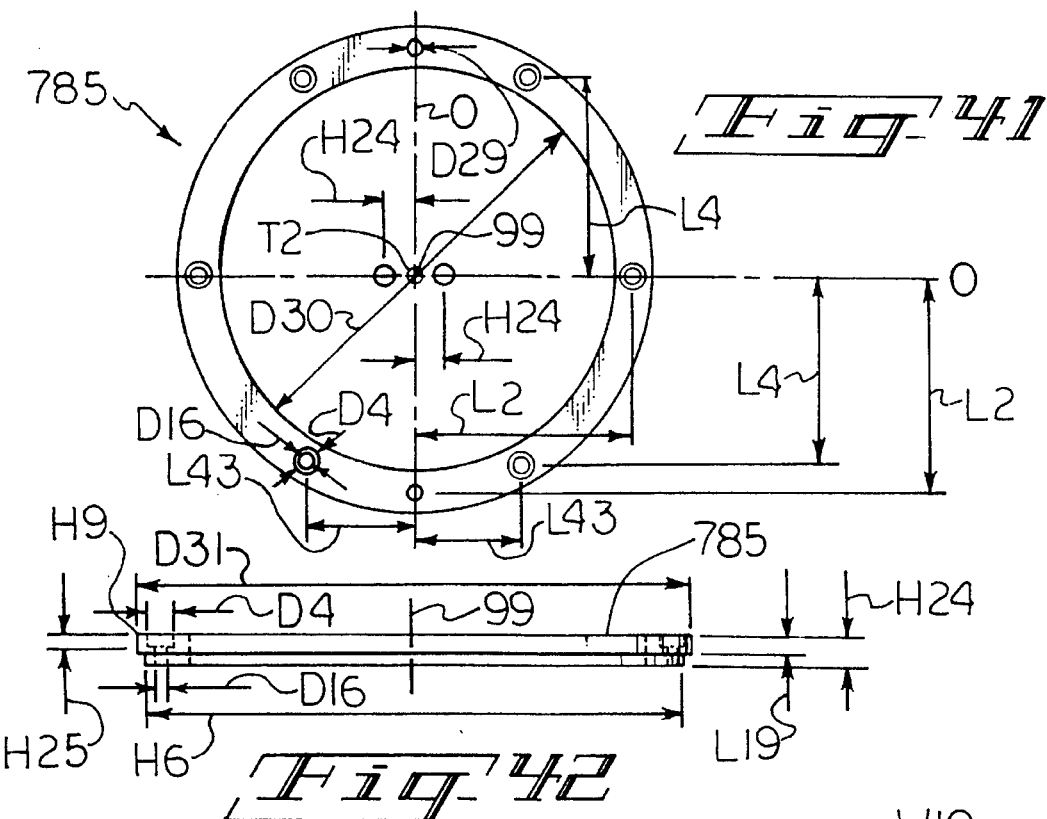
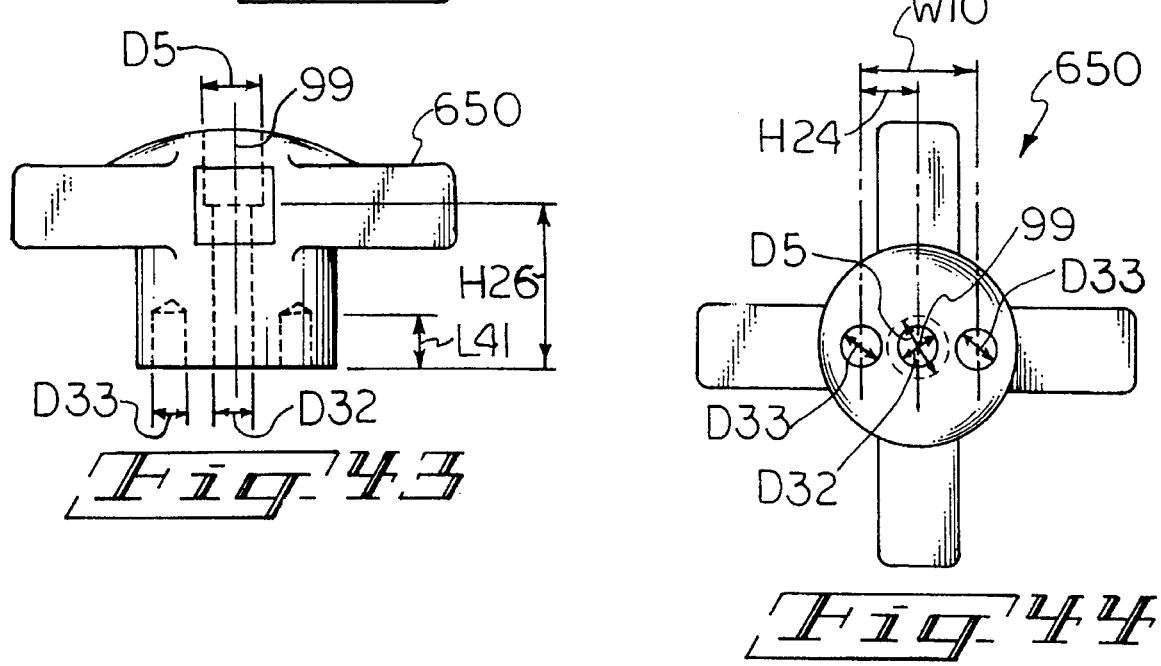

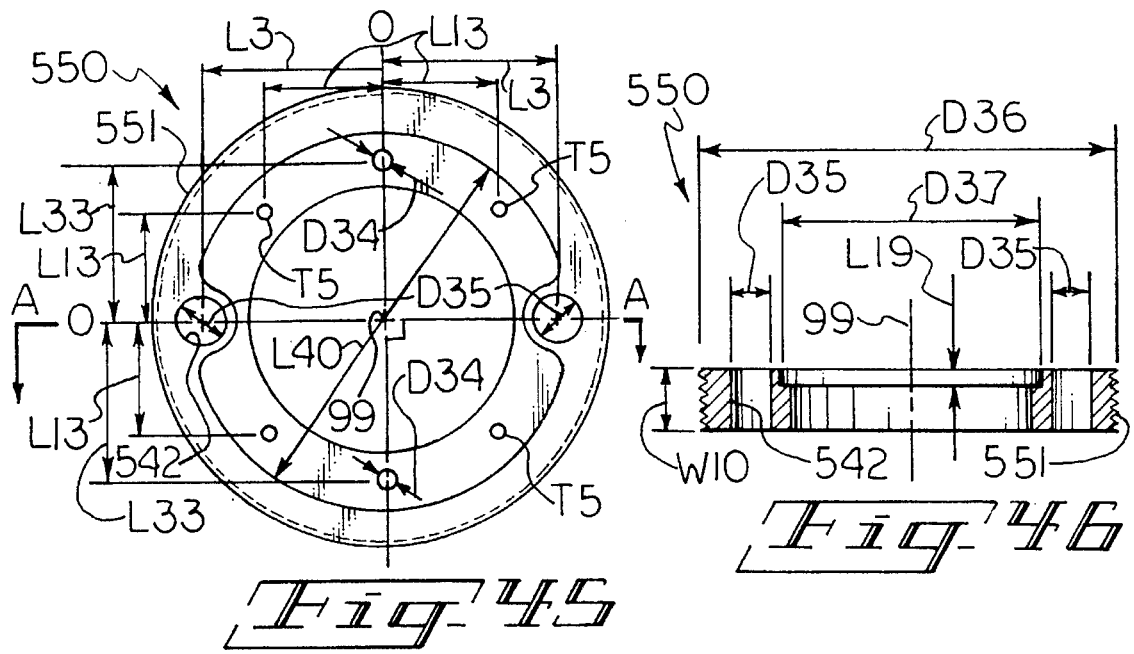
Fig 45
Fig 46
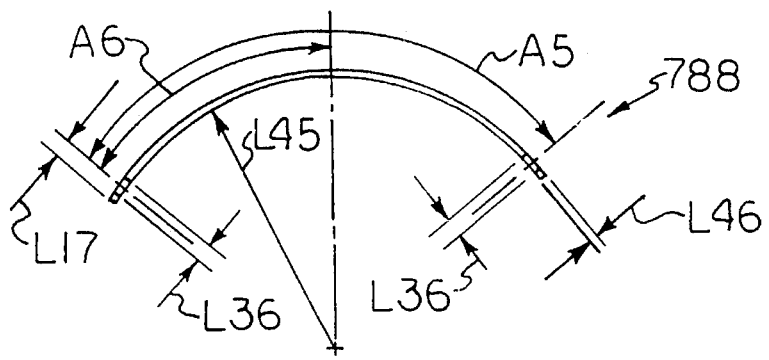
Fig 47
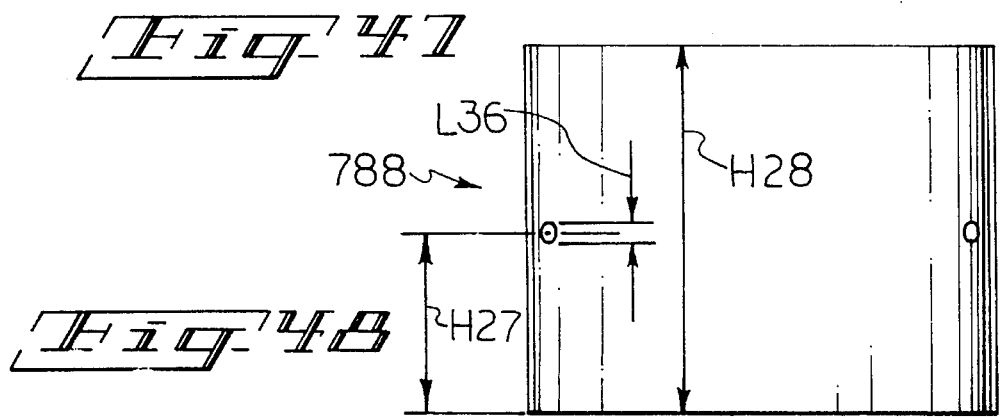
Fig 48

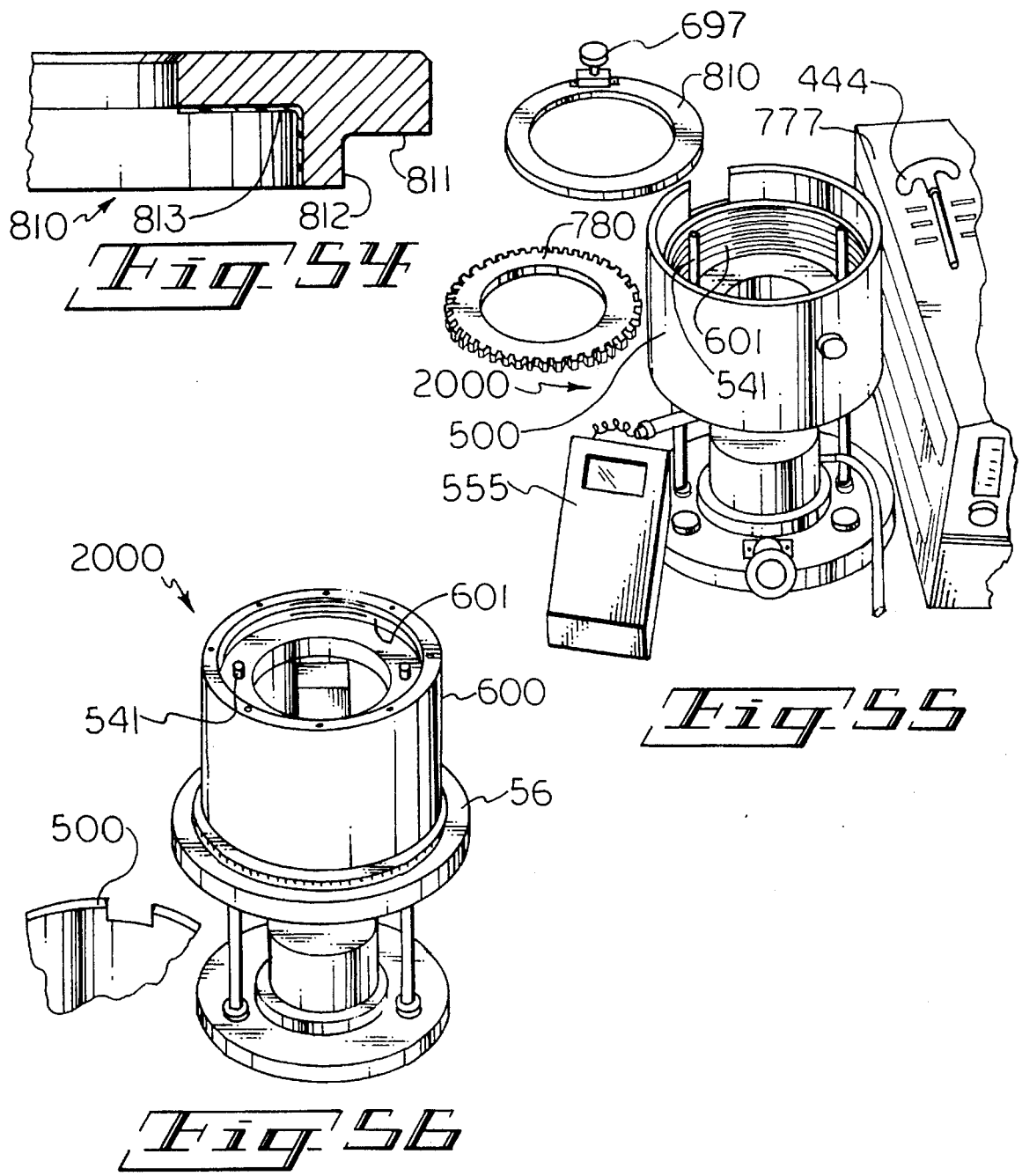

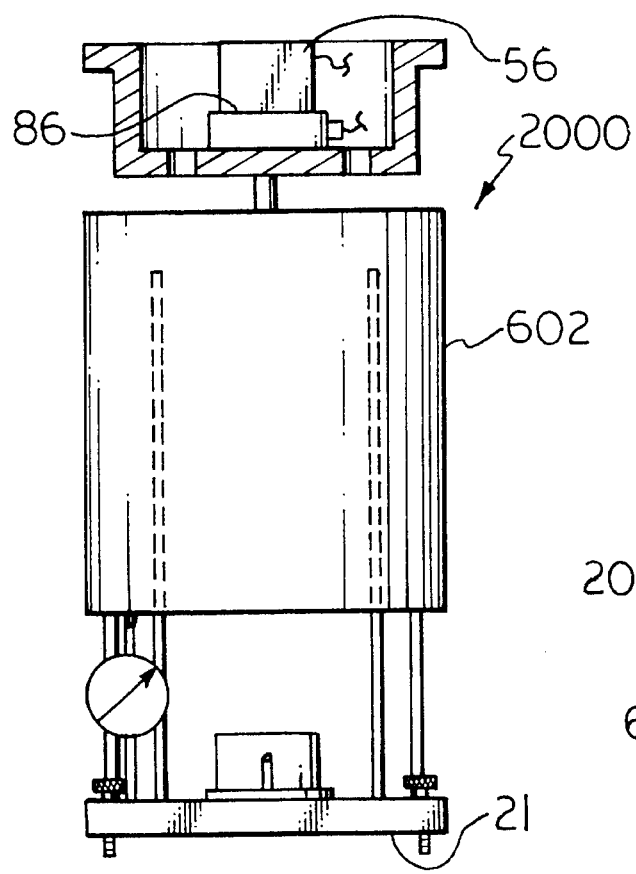
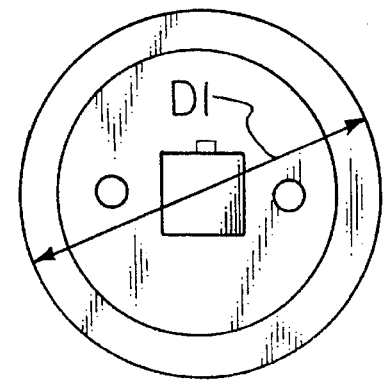
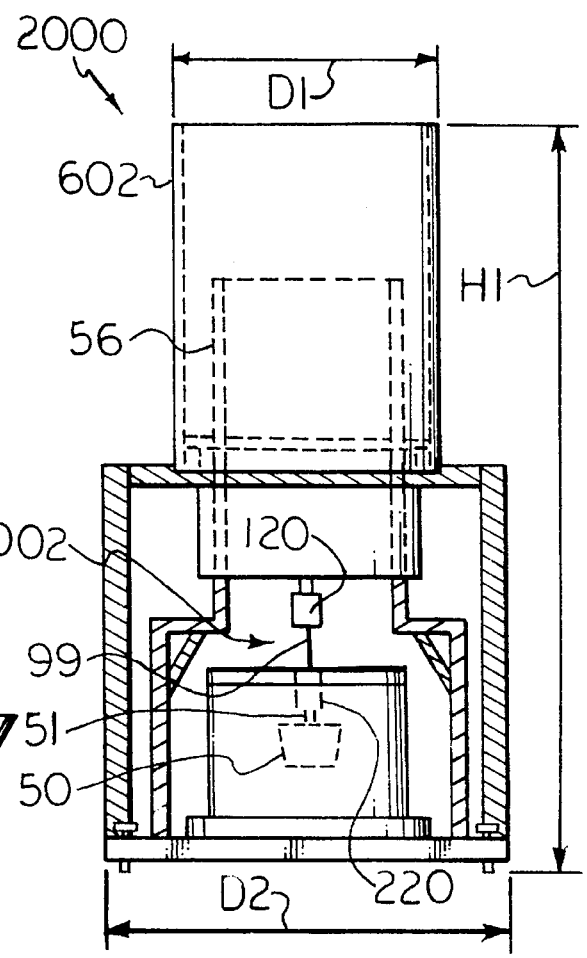

STACKED COMPONENT TAPERED BEARING SIMULATOR DEVICE

FIELD

This invention concerns an instrument and method for measuring the resistive force of elements to include the viscosity of fluids. More particularly, it concerns improvements in a rotational device such as a dynamometer or most particularly a viscometer, the latter being a type of the former, having a tapered rotor-stator geometry such as is useful for testing lubricating oils and other liquids at high shear in a shearing environment similar to that of a journal bearing in the engine of a motorized piece of equipment including an automotive engine.

BACKGROUND

In general, in tribology, the characteristics of fluids are of notable practical concern and a cause for much study. In the automotive industry especially, it is important to be able to determine and predict the viscosity and performance characteristics of an engine oil or other lubricants without having to test the same in an actual engine or other working mechanism. Further as well, in the printing industry, the characteristics of printing inks can be of critical concern.

Several rotational viscometers have been developed, which are intended, among other things, for studying such non-Newtonian fluids as multigrade motor oils formulated by blending viscosity index improvers, synthetic polymers, and so forth, into straight mineral oils. See, Kim et al., U.S. Pat. No. 3,350,922 (Nov. 7, 1967), and W. C. Pike et al., "A Simple High Shear Viscometer," SAE Publication No. 780981 (1978). Generally, such instruments, although useful, are complex, expensive, sometimes unstable, and reliable only in the hands of qualified scientists.

In ameliorating or overcoming such problems as these, Theodore W. Selby invented and disclosed a tapered bearing simulator-viscometer, U.S. Pat. No. 4,445,365 (May 1, 1984). It is characterized by simple, benchtop operation, and its commercial embodiments, available from Tannas Co., Midland, Michigan, U.S.A., are believed to be the only very high shear (100,000 per reciprocal second and beyond) absolute viscometers commercially available—shown in ASTM studies to be the most accurate and precise of known very high shear rate viscometers, thus being suitable for production control as well as an excellent research tool. Organic and water based liquids, including engine oils, automatic transmission fluids, hydraulic fluids, waxes, and polymeric solutions have been tested on the tapered bearing simulator-viscometer at viscosities ranging from 1 to 100 centipoise (cP) depending on the temperature and shear rate. See, e.g., Tannas Co., catalog, pages 2 & 3 (1994).

Be that as it may, even the highly successful tapered bearing simulator-viscometer of Mr. Selby has its drawbacks. Chief among these are the following:

1) A hystersis synchronous motor is used, in which rotational speed is proportional to the frequency of the alternating current electrical input. For example, with an alternating current of 60 cycles per second, the motor speed is 3600 rotations per minute (rpm). However, if electrical devices, as for example, a refrigeration compressor, are operated on the same circuit, a change in the the number of cycles per second of the alternating current may occur. This in turn causes the motor speed to fluctuate, which in turn causes torque to fluctuate, which causes the instrument readout related to viscosity to fluctuate inaccurately.

2) The motor is housed in a motor housing which is supported on a turntable assembly in a platform and which rotates within a limited arc; supporting the turntable are eight ball bearings in a circular race. The bearings in this arrangement can drift and/or get dirty, causing the turntable/housing to lean, which in its turn also causes the instrument readout related to viscosity to shift inaccurately.

3) The motor is fed electricity through lead wires. The lead wires, which are external to the motor housing, and may dangle, can tug or pull, thus creating unpredictable drag not related to fluid viscosity, which in turn causes the torque values to shift, which causes the instrument readout related to viscosity to shift inaccurately.

4) The motor, rotor and stator assembly is supported on the platform, which is cantilevered from a slide plate as its only support. This arrangement can cause slight alignment problems, which in turn causes the torque and so forth to shift, which causes the instrument readout of viscosity to fluctuate inaccurately.

Although the inaccuracies caused by such arrangements of the Selby tapered bearing simulator-viscometer can be small, greater and greater accuracy and precision is being demanded in the viscometry art. See, e.g., Hydrock, "Automotive Lubricant Test Standards Keep Tightening," *Lubricants World,* Vol. 4, No. 12, pages 7, 10–11 & 14 (Dec. 1994).

It is desirable, accordingly, to overcome such problems, and be able to provide even more accurate and precise ways and means to measure fluid viscosity.

SUMMARY

The present invention provides a stacked component tapered bearing simulator device comprising a stator block having a sample receiving bore; a rotor complementary to the stator block bore extending axially into the bore to define therebetween a thin measuring gap, the rotor having a drive shaft extending axially upward from it; a motor housing, which can rotate in response to torque or drag from a test sample present in the measuring gap, including a motor which drives the shaft and rotor around an axis of rotation; a means for sensing the torque, which is fixable to the motor housing, and which is connectable to a platform that is vertically adjustable by an elevator mechanism, which generally, externally bounds the axis of rotation of the motor, drive shaft, and rotor—preferably comprising a threaded arrangement with an anti-rotation device wherein one set of threads resides with the platform, which is restrained from rotating by the anti-rotation device but allowed to be moved vertically, and another set of threads for mating with said one set of threads resides with at least one rotatable member separate from but threadedly engagable with said one set of threads of the platform. Accordingly, from the principles of the foregoing, more broadly provided is a stacked component force measuring device comprising an element to provide a resistive force for measurement; a rotor in communication with the element, the rotor having a drive shaft extending axially from it; a motor housing, which can rotate in response to torque or drag from the element, including a motor which drives the shaft and rotor around an axis of rotation; a means for sensing force with respect to the element, which is fixable to the motor housing, and which is connectable to a platform that is adjustable in a direction of the axis of rotation by a linear translocating mechanism, which generally, externally bounds the axis of rotation of the motor, drive shaft, and rotor. Other provisions may include a direct current motor to ameliorate or eliminate speed fluctuation possibilities, low-interference motor and load cell connections, an in-line load cell, and/or other specific embodiments.

The invention is useful in dynamometry, to particularly include viscometry. In preferred embodiments thereof, it is especially useful in determining fluid viscosities according to the well-known ASTM D 4683 protocol.

Significantly, by the invention, problems such as those mentioned in the foregoing background section are overcome, eliminated, or ameliorated. Accordingly, a new generation of tapered bearing simulator viscometry instrumentation is provided, which can employ a stacked component arrangement and other features for highly stable operation, and high accuracy and precision of test sample viscosity data. What is more, the invention may be more broadly applied. The invention is most amenable to being fully automated.

Numerous further advantages attend the invention.

DRAWINGS

The drawings form part of the specification hereof. In the drawings, which are not necessarily to drawn to scale or may not correspond in scale from one figure to another, and in which like numerals refer to like features, the following is briefly noted:

FIG. 1 is a front, partial cut away view of a tapered bearing simulator viscometer of the present invention, which employs an analog micrometer.

FIG. 2 is a side view of the viscometer of FIG. 1.

FIG. 3 is a front perspective view of another tapered bearing simulator viscometer of the present invention, which employs a rotating member as part of the elevator mechanism thereof, the so-called "adjusting nut," and a micrometer and vernier scale in conjunction therewith.

FIG. 7 is a top plan view of the viscometer as depicted in FIG. 4.

FIG. 8 is a section view of the viscometer as depicted in FIG. 5, taken along B—B.

FIG. 9 is a section view of the viscometer as depicted in FIG. 4, taken along C—C.

FIG. 10 is a section view of the viscometer as depicted in FIG. 4, taken along D—D.

FIG. 11 is a top view of a base plate of the viscometer from FIGS. 3–10.

FIG. 12 is a side view of the plate of FIG. 11.

FIG. 18 is a top view of an upper adapter plate from the viscometer of FIGS. 3–10.

FIG. 19 is a side view of the plate of FIG. 18.

FIG. 20 is a top view of a lower adapter plate from the viscometer of FIGS. 3–10.

FIG. 21 is a side view of the plate of FIG. 20.

FIG. 22 is a side view of the drive motor from the viscometer of FIGS. 3–10. See, e.g., FIG. 6.

FIG. 33 is a top view of a retainer ring from the viscometer of FIGS. 3–10.

FIG. 34 is a side, cut-away view of the ring of FIG. 33.

FIG. 35 is a top view of a static housing from the viscometer of FIGS. 3–10.

FIG. 36 is a side, partial cut-away view of the housing of FIG. 35.

FIG. 37 is a top view of the adjusting nut from the viscometer of FIGS. 3–10.

FIG. 38 is a side, cut-away view of the nut of FIG. 37.

FIG. 39 is a top view of a drive gear from the viscometer of FIGS. 3–10.

FIG. 40 is a side view of the gear of FIG. 39.

FIG. 41 is a top view of a drive plate from the viscometer of FIGS. 3–10.

FIG. 42 is a side view of the plate of FIG. 41.

FIG. 43 is a side view of a hand adjusting knob from the viscometer of FIGS. 3–10.

FIG. 44 is a bottom view of the knob of FIG. 43.

FIG. 45 is a top view of an adjusting screw from the viscometer of FIGS. 3–10.

FIG. 46 is a side section of the screw of FIG. 45, taken along A"–A".

FIG. 47 is a top view of an access cover from the viscometer of FIGS. 3–10.

FIG. 48 is a side view of the cover of FIG. 48.

FIG. 54 is an enlarged side, cut-away view of part of the cover of FIGS. 52 & 53, taken within circle A' of FIG. 53.

FIG. 55 is a top, front perspective, partially exploded, view of a partially disassembled viscometer as depicted in FIG. 3, including geared, screwing height adjuster, and a modified outer housing for accommodating the gear-actuated, screwing height adjuster, and so forth.

FIG. 56 is another perspective view of a viscometer as of FIGS. 3 & 55, partially disassembled, and having its static, outer housing removed.

FIG. 57 is a side view of another viscometer of the invention, without a static, outer housing.

FIG. 58 is a top plan view of of a top portion of the viscometer as depicted in FIG. 57.

FIG. 59 is a side plan view of the viscometer as depicted in FIGS. 56 & 57.

ILLUSTRATIVE DETAIL

The invention is further illustrated with the following detail, which generally may be taken in conjunction with the drawings, and is not to be construed as limiting in nature.

The device of the invention can be generally embodied in a dynamometer. Preferably, the device is a viscometer.

Patents mentioned herein are incorporated by reference.

The invention may be considered to be an improvement of the aforementioned tapered bearing simulator-viscometer of U.S. Pat. No. 4,445,365 to Selby, sold by the Tannas Co., Midland, Mich. Particularly preferred improvements concern or replace its elevator mechanism, and also may concern or replace its turntable bearing arrangement, its electrical motor, its specific electrical connections, and so forth.

Figure 63:
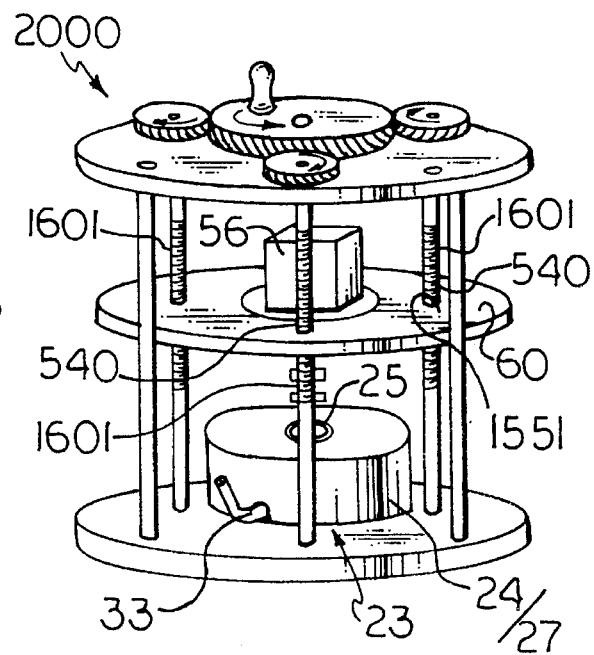
FIG. 63 is a perspective view of a viscometer of the invention having yet another alternate threaded arrangement with an anti-rotation device comprising threaded rods.

In reference to the drawings, particularly FIGS. 1–63, stacked component tapered bearing simulator viscometer 2000 generally includes, such as with the aforementioned tapered bearing simulator-viscometer of U.S. Pat. No. 4,445,365, a base plate 21, a viscometric test cell 23 having housing 27 and stator block 24 having sample receiving bore or well 25, fill tube 33, overflow outlet 38, temperature-regulating fluid inlet 43 and outlet 49, and so forth, and having rotor or drum 50 complementary to the bore 25 extending axially into the bore to define a thin measuring gap between the bore 25 and drum 50. The rotor 50 has drive shaft 51 extending axially upward from it. Motor 56, the housing of which can rotate in response to torque or drag from a test sample such as an oleaginous liquid, for example, engine oil, transmission fluid, etc., present in the thin measuring gap, drives the shaft and rotor around axis of rotation 99. A means for sensing torque 86 is fixable to the motor housing, in which is included shaft-and-rotor driving parts to make a motor, with the motor housing with its motor in assembly at times referred to generally as the motor 56 as the surrounding context reveals, and the means for sensing torque 86 is connectable to a platform 60 which is vertically adjustable by linear translocating or elevator mechanism 600. In general, this mechanism 600 externally bounds the axis of rotation of the motor 56, drive shaft 51, and rotor 50, i.e., axis of rotation 99.

Fill tube support 331 may support fill tube 33.

Preferably, although other elevating mechanisms such as a pneumatic lift, hydraulic lift, jack lift or other lever lift, sliding wedge lift, chain or filamentous containing lift, or other mechanical lift, thermally expanding material lift, and so forth, may be employed in the viscometer of the invention, the elevator mechanism 600 includes a threaded arrangement with an anti-rotation device. Therein, one set of threads, for example, male thread set 551 as seen in FIGS. 4–6, 45 & 46, may reside with the platform 60 or its environs connected therewith, for example, to include an adjusting screw 550, for example, made from No. 1018 cold rolled steel, which is restrained from rotating by the anti-rotation device 540 that may be embodied in a set of guide shafts 541, and another set of threads, for example, female thread set 601 of adjusting nut 602, for example, made from a steel tube, as seen in FIGS. 1, 4–6, 10, 37, 38, 55–57, 59, 60 & 62, for mating with said one set of threads may reside with at least one rotatable member separate from but threadedly engagable with said one set of threads which may reside with the platform 60. As an alternative example, the one set of threads which may reside with the platform 60 or its environs connected therewith may be female thread set 1551, and the other set of threads for mating with the female thread set 1551 may be male thread set 1601, as can be appreciated from FIG. 63. Operation of the elevator mechanism 600 can raise and lower the motor 56, for example, raising it to elevated position 56e as illustrated within FIG. 6, along with the drive shaft 51 and the test drum 50 in the sample bore 25.

Preferably, the bore 25 is frusto-conical.

Preferably, the motor 56 is co-axial with direct drive.

Preferably also, the viscometer of the invention employs as the motor 56, a direct current (DC) electric motor. For example, such a DC motor may be a commercially available Pittman Motor Model No. 4111, WDG No. 1, HEDS-9100, 100 PPR, with a 2½-inch (6.35-cm) long shaft. Such a motor has low-interference electrical connections, eliminating wiring which may drag, act as an undesired spring, and/or catch on nearby viscometer features, equipment or even operators.

Preferably, the viscometer of the invention employs as a portion of the drive shaft 51 a series cojoined collet shaft Mr. Theodore W. Selby invented and disclosed in U.S. Pat. No. 5,369,988 (Dec. 6, 1994). Advantageously, the cojoined collet shaft employed is a double cojoined collet flexible shaft 1002, including a first cojoined collet 120 with first collet nuts 130, a flexible wire shaft 10, and a second cojoined collet 220 with second collet nuts 230. The same is commercially available from Tannas Co., Midland, Mich.

Preferably, the viscometer of the invention employs a load cell as the means to sense torque 86, and the load cell is desirably an in-line load cell. For example, the in-line load cell 86, which generally is coaxial with the motor 56 along axis of rotation 99, and connectable with the motor 56 or that is to say connecting the motor 56 with platform 60 at least indirectly if not directly, may be a commercially available ISR Transducer Div., RTS Series reaction torque sensor Model No. RTS-XXXZ. The motor 56 may mount on the in-line load cell 86 through an adapting plate 710 as, for example, provided by a combination of a lower adapter plate 718 and an upper adapting plate 719. See, FIGS. 5, 6 &

17–21. The assembled motor 56 and in-line load cell or transducer 86 may be mounted on platform transducer mount 720 which may be considered to a part of or be connected to platform 60 as by means of transducer housing or shell 740 through adjusting screw 550. See, FIGS. 4–6, 15–17, 23–26, 27, 45 & 46.

Figure 5:
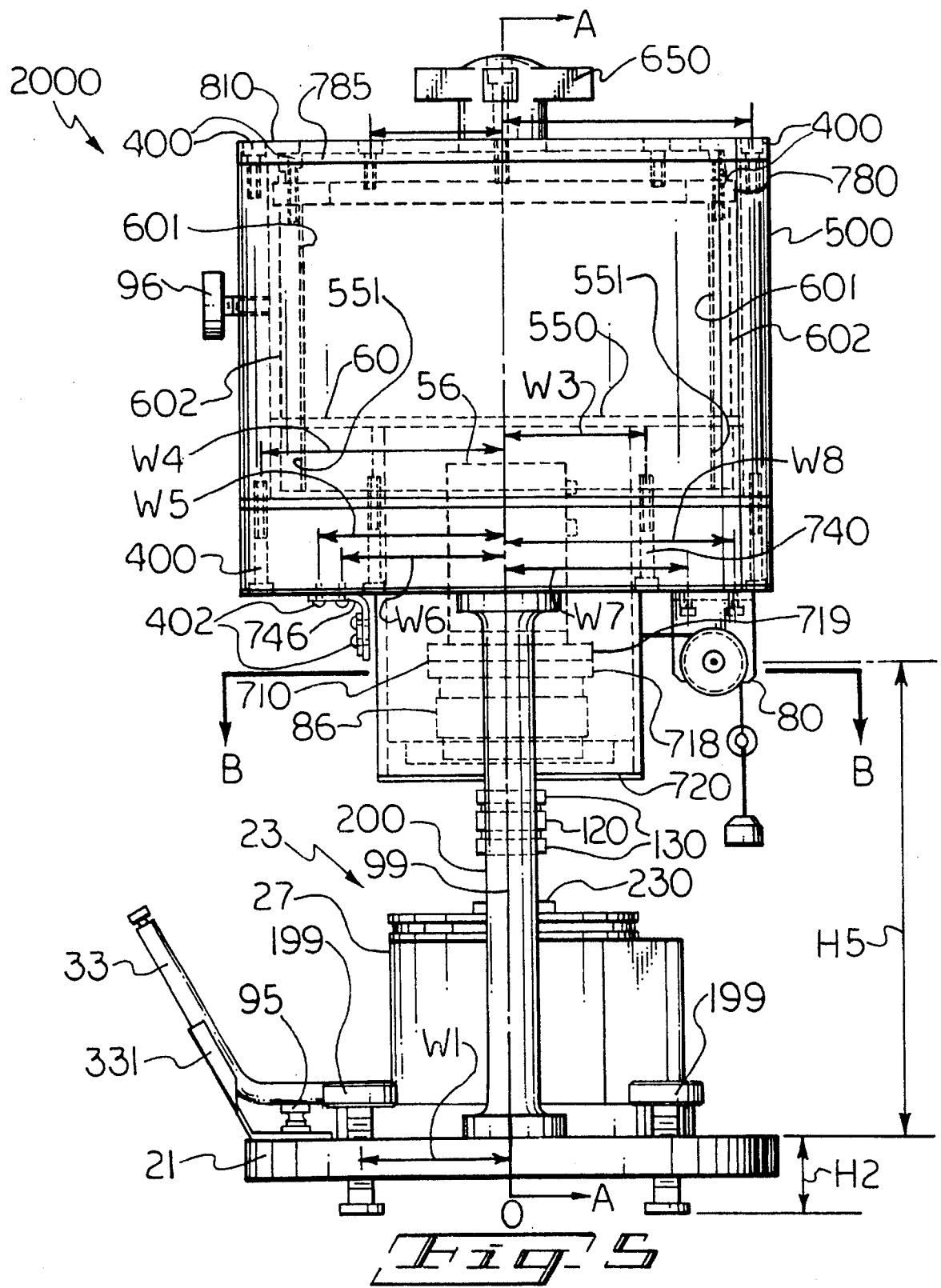
FIG. 5 is a side elevation view of the viscometer as depicted in FIG. 4.
Figure 27:
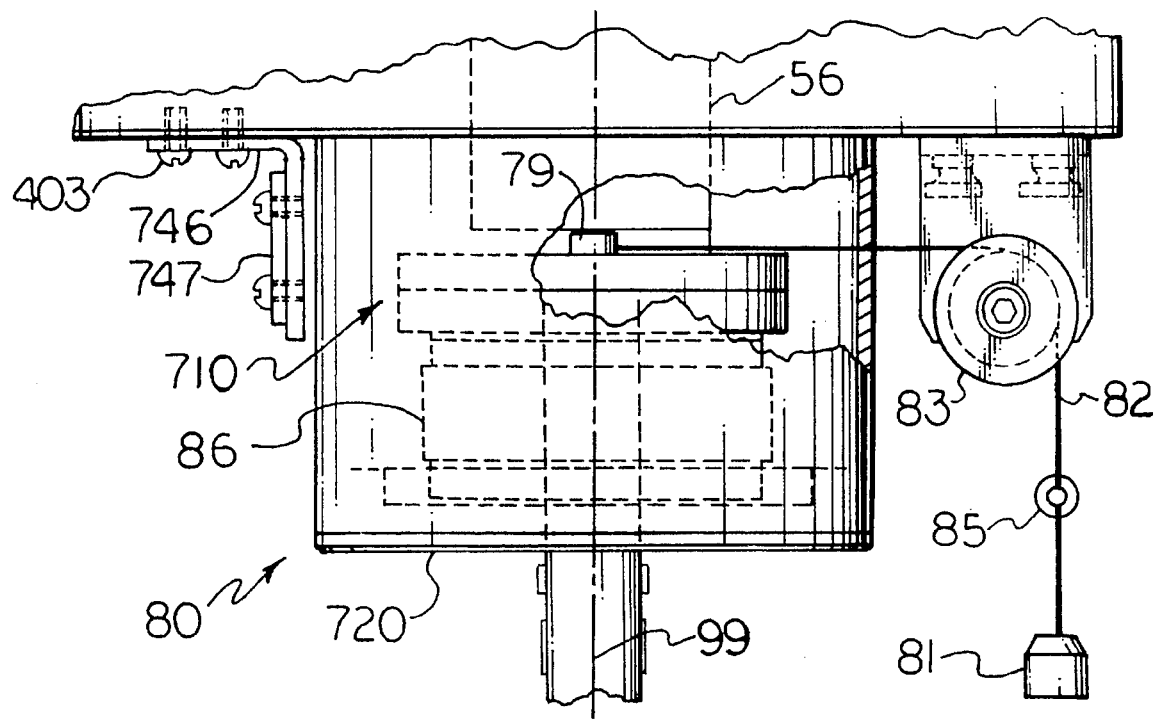
FIG. 27 is a partial cut away, side elevation view of part of the viscometer of FIGS. 3–10, as depicted in FIG. 5, focusing on its pre-load assembly.
Figure 28:
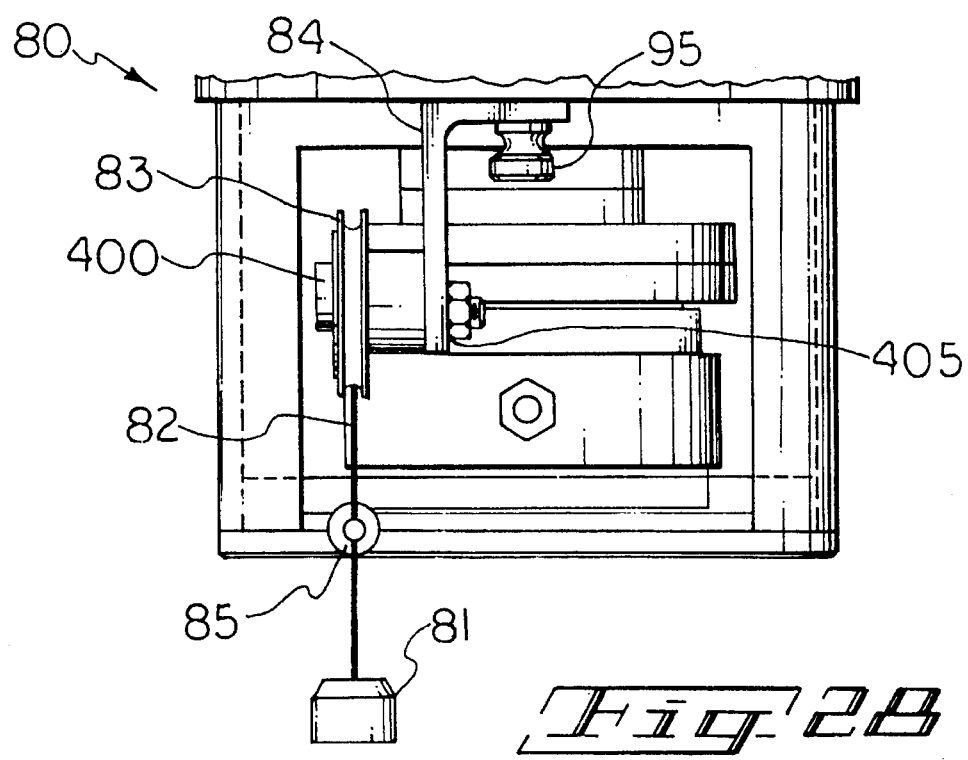
FIG. 28 is a rear view of the pre-load assembly part of the viscometer as depicted in FIGS. 5 & 27.

Preferably, as depicted in FIGS. 5, 27 & 28, pre-load assembly 80 is present. This assembly 80 is generally that of the Selby patent (q.v.) or similar thereto.

Connections may be made between or among components such as by means of fasteners, for example, dowels and/or screws, or any other suitable means. For instance, in appropriate circumstances, gluing, welding, pinning, press-fitting, and so forth may be employed to make component connections. A tool such as screw tool 444 may be employed (FIG. 55).

Metal parts are generally desirable although any suitable material may be employed. This chiefly depends upon the function and characteristics required of a component, as those skilled in the art appreciate.

Component parts may be made by known methods. For instance, with metal or suitable plastic components, casting, forging, molding, rolling, bending, cutting, drilling, lathe-cutting, polishing, scribing, and so forth and the like may be employed.

Further, the following is noted:

In FIGS. 4–6, 10 & 11 is presented more detail of the base plate 21. This plate 21, for example, of aluminum, may hold the viscometer test cell 23 such as with thumb screws 95 and upper viscometer components through support rods 200, for example, by means of support rod base supporting cup 221 and suitable fasteners such as a socket head cap screw 400 passing through support rod base supporting hole 222. The base plate 21 may be adjusted to level the viscometer with leveling screws 199, for example, four commercially available Carr-Lane swivel head screws, No. CL-21-SHSN.

In FIGS. 4–6, 9, 13 & 14 is presented more detail of the support rods 200. Such a rod 200, for example, of aluminum, may fit into the base 21 as aforesaid, and connect with the viscometer upper components through mid-plate 760 to include parts as noted in due course below.

In FIGS. 4–6 & 15–17 is presented more detail of the transducer mount 720. Such a mount 720, for example, of aluminum, can connect with transducer shell 740 and in-line transducer 86, for example, by use of suitable screws such as countersunk flat head screws 401 or other suitable screws. It may have lower lip 721 and inside ridge 722 to hold it in place with the shell 740, and transducer-mounting cup 723. Onto the transducer mount 720 is mounted the transducer 86. In FIGS. 5, 6 & 18–21 is presented more detail of the adapter plate 710. This plate 710 may be assembled from two plate components, upper adapter plate 719 and lower adapter plate 718, depicted in FIGS. 18–19 & 20–21, respectively. Such plates 718 & 719, for example, may be made of aluminum, and be connected by suitable fasteners such as screws 400. This plate assembly is mounted on the transducer 86, and it connects the motor 56 therewith, for example, by screws 400.

Figure 6:
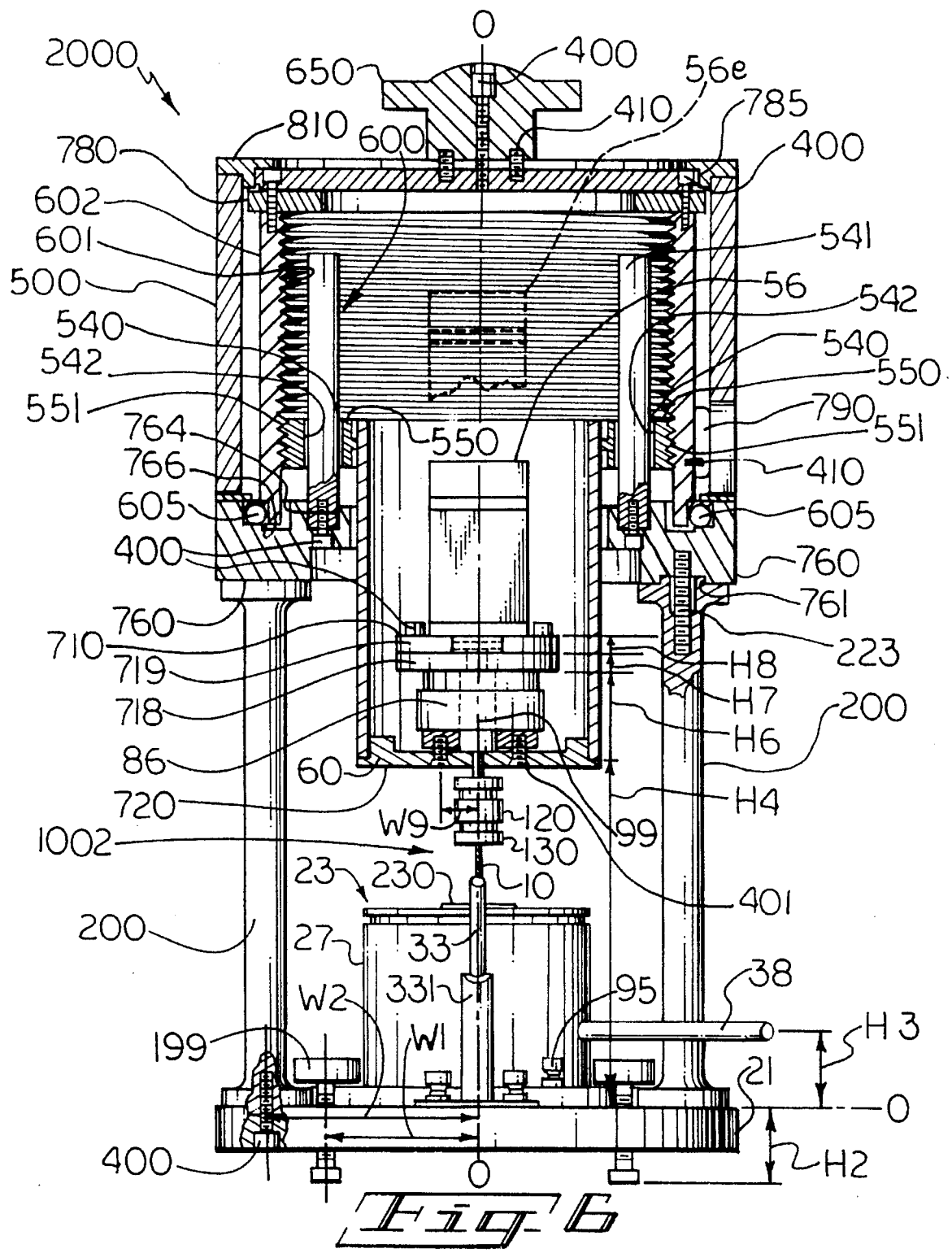
FIG. 6 is a section view of the viscometer as depicted in FIG. 5, taken along A—A.

In FIGS. 5, 6 & 22 is presented more detail on motor 56.

In FIGS. 4–6 & 23–26 is presented more detail of the transducer shell 740. Such a shell 740, for example, made from aluminum tubing, can connect upper and lower platform parts of the platform 60, for instance, the adjusting screw 550 and transducer mount 720. The shell 740 may have window 741, lip 742 and recesses 743. General height-indicating indicia may be a series of engraved numbers 744 and scribed lines 745, for example, being scribed every 1 millimeter (mm) with longer scribes at each 5-mm position, filled with a recognizable material such as a paint contrasting in color to the color of the shell 740, for example, white and black.

Figure 4:
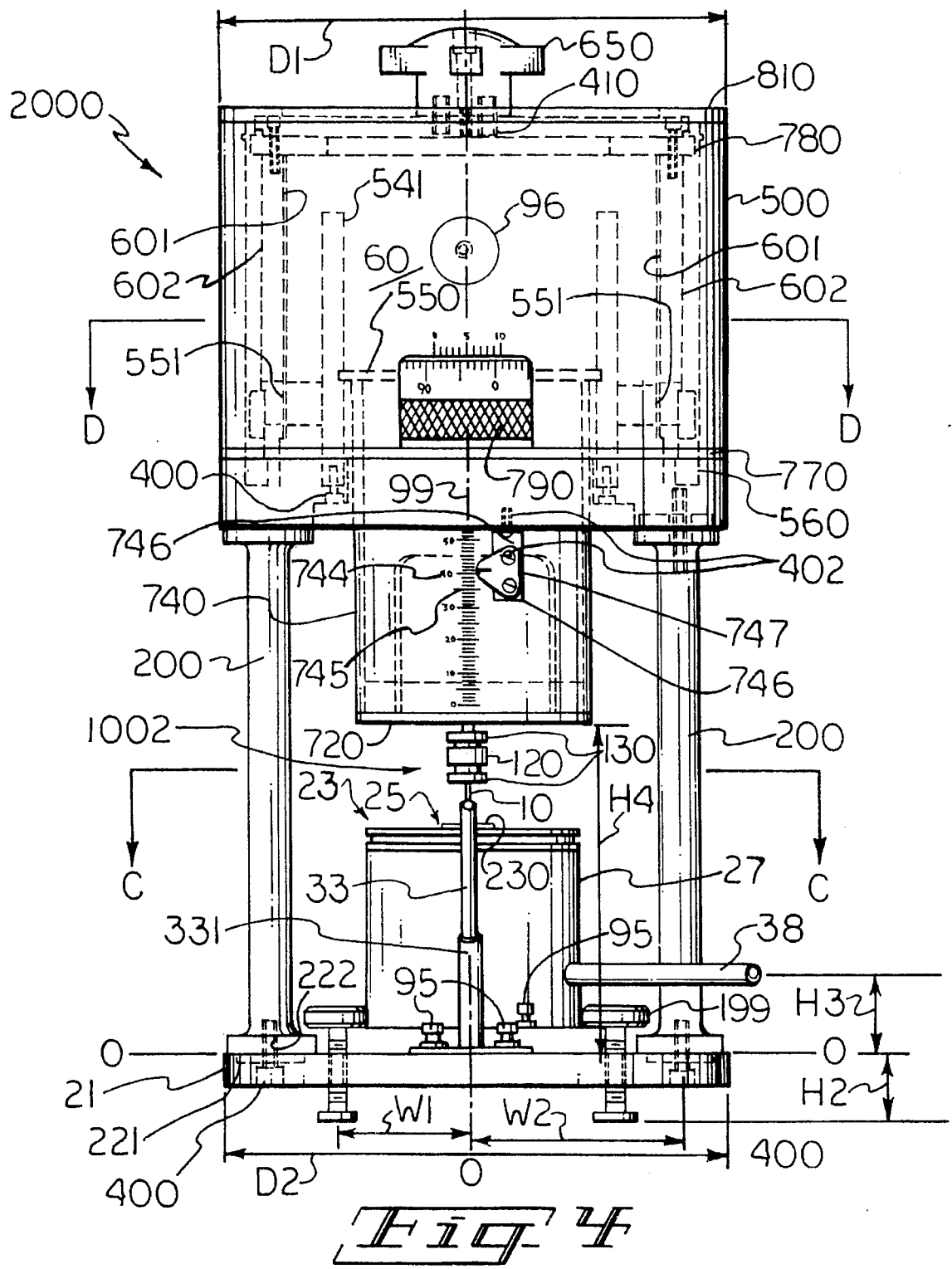
FIG. 4 is a front elevation view of the viscometer as depicted in FIG. 3.

In FIGS. 4, 5 & 27 is presented detail of indicator bracket 746 and assembly. This bracket 746, for example, a pulley bracket, may be connected with round-head screws 402 to the transducer shell 740 and mid-plate 760. Adjustable indicator plate 747 holds indicator index 748 for reading the general height-indicating indicia with lines 745.

In FIGS. 5, 27 & 28 is presented more detail of the pre-load assembly 80. Like the pre-load assembly of the aforementioned Selby patent, pre-load assembly 80 applies predetermined torque in the direction opposite to that in which the motor 56 turns, and it includes a predetermined weight 81 hanging from line 82 which goes over a pulley 83 and is looped around a stop post 79. The pulley 83 is held at the end of pulley bracket 84, and fiber washer 85 may assist in replacement of variously-weighted weights 81. Assembly may be assisted with employment of a socket head cap screw 400, complementary nut 405, and thumb screw 95.

Figure 29:
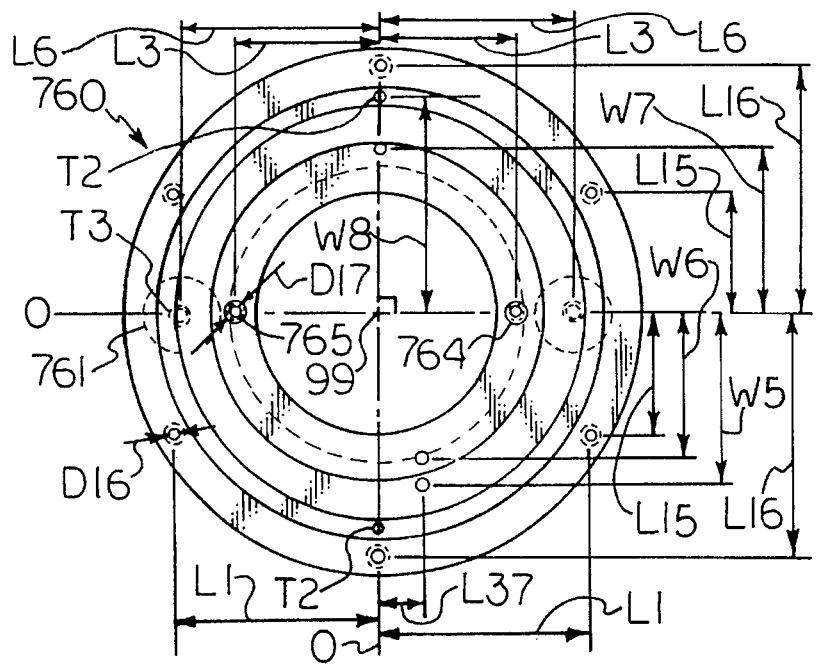
FIG. 29 is a top view of a mid-plate from the viscometer of FIGS. 3–10.
Figure 30:
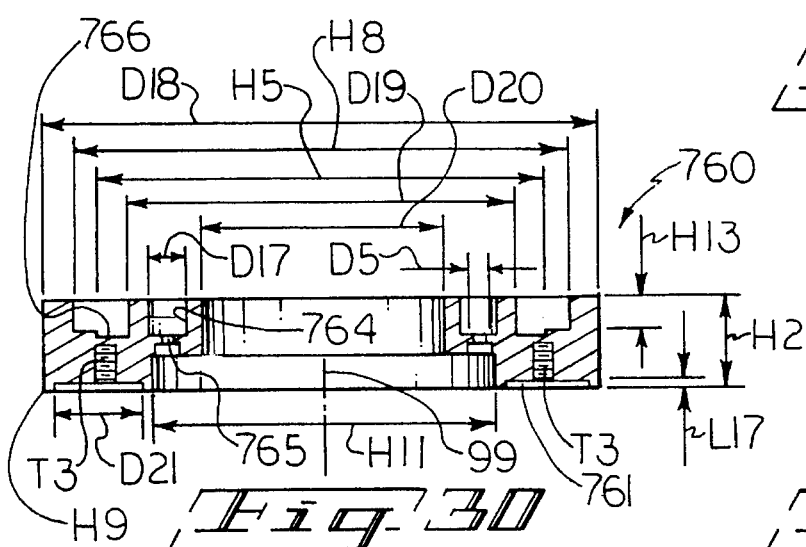
FIG. 30 is a side view of the mid-plate of FIG. 29.
Figure 32:
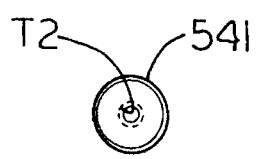
FIG. 32 is a bottom view of the shaft of FIG. 31.

In FIGS. 6, 29 & 30 can be seen more detail of the mid-plate 760. Such a plate 760, for example, of stainless steel, may include a guide shaft cup 764 for retaining the guide shaft 541, which may be fastened with a suitable fastener, for example, suitable socket head cap screw 400, passing through mid-plate guide shaft hole 765. Included also may be support rod upper cup 761 to accept support rod 200 which may be fastened with a fastener, for example, a suitable screw such as a support rod stud screw 223. Also included may be adjusting nut and bearing groove 766 for holding adjusting nut 602 and bearing 605 such as, for example, an SKF Bearing, Slimline four-point contact ball bearing ring with seals, No. FPAJ 608 RS1, as in FIG. 6.

In FIGS. 4, 6, 31 & 32 is presented more detail on the guide shaft 541. The shaft 541 may be made, for example, of No. 1018 steel shafting.

In FIGS. 5, 6, 33 & 34 is presented detail of a retainer 770. The retainer 770, for example, of aluminum, assists in alignment and retention of static outer housing 500, bearing 605, and so forth.

In FIGS. 4–6, 35 & 36 is presented more detail of the static outer housing 500. This housing 500, for example, made from aluminum tubing, may have upper access window 501, lower readout access window 502, and large thumbscrew 96 for holding fast the adjusting nut 602 when the operator is satisfied that a desired height is reached. Fine indicia 505 for vernier scale height readout may be provided, for example, with zero-to-ten readout lines scribed every 1.62 degrees and filled with a recognizable material such as a paint contrasting in color to the color of the housing 500, again, for example, white and black.

Figure 60:
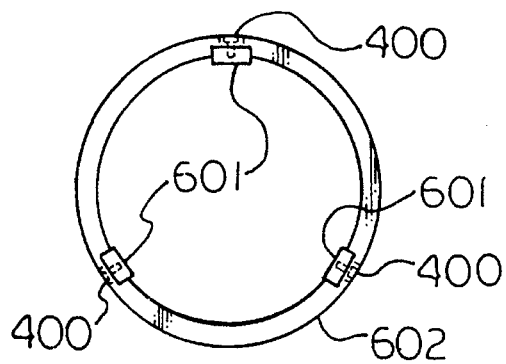
FIG. 60 is a top view of an alternate threaded arrangement such as in an adjusting nut of the invention.
Figure 61:
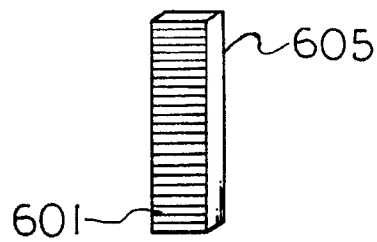
FIG. 61 is a view in elevation of a threaded bar insert insertable into the arrangement of FIG. 60.
Figure 62:
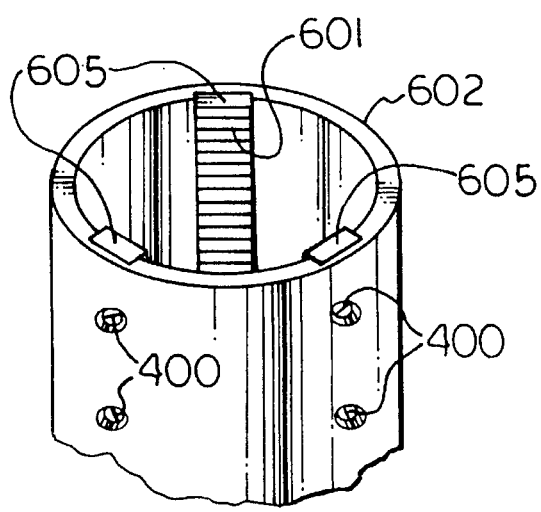
FIG. 62 is a perspective view of the arrangement as of FIG. 60.

In FIGS. 4–6, 37, 38 & 60–62 is presented more detail of the thread 601—containing, adjusting nut 602. This nut 602, for example, made of steel tubing, may have threads 601 tapped inside such a tube, for example, M150×2–6H precision threads (FIGS. 4–6, 37 & 38). Alternatively, to serve to help lower the friction of turning adjusting screw 550 with a substantial portion of its circumference devoted to threads 551 therein, a tube may have several upraised portions upon which precise threads 601 are cut, which may be provided by simply cutting away portions of threads in such a tube or, for instance, by providing separable bars 605.(FIGS. 60–62)

in which the threads 601 are cut. The bars 605 may be adjustable vertically and spring-loaded (not depicted), for instance, with a downward bias, so that the bars force the adjusting screw threads 551 to the bottom of the cut groove or thread 601 to increase the stability of a platform 60. The bars 605 may be screwed in place by screws 400 at a desired height. Upper shoulder 607 may have a 0.03-inch (0.76-mm) maximum radius, and lower shoulder 608 may have a 0.01-inch (0.25-mm) maximum radius.

In FIGS. 4–6, 39 & 40 is presented detail of drive gear 780. The gear 780, for example, may be a commercially available gear, and it may be connected to the adjusting nut 602 by suitable socket head cap screws 400.

In FIGS. 4–7, 41–43 is presented detail of a drive plate 785 and hand knob 650 for turning adjusting nut 602. The plate 785 may be, for example, of aluminum, and the knob 650 may be commercially obtained. Screws 400 and dowels 410 may hold these components together and to the nut 602.

In FIGS. 4–6, 45 & 46 is presented more detail of the adjusting screw 550. The screw 550 may be, for example, made of No. 1018 cold rolled steel, with M150×2–6 g threads 551. The screw 550 may also include guide post sleeve 542, for example, of a bronze bunting bushing. As an alternative to reducing the contact area of threads on the adjusting nut 602 for lowering friction as discussed above, the threads 551 may be interrupted to lower friction of adjusting the height of a screw-type elevator mechanism 600. In FIGS. 8, 47 & 48 is presented detail of an access cover 788. The cover 788 may be, for example, of aluminum.

In FIGS. 4 & 49–51 is presented detail of a knurled ring 790. The ring 790, for example, made of steel tubing, may have a medium diamond knurl 791 for making sensitive height adjustments, and scribed indicia, for example, numbers 792 and lines 793. The numbers 792 may start at zero at positions 794 and register fifty at positions 795. The lines 793 may be scribed every 1.80 degrees. The numbers and lines may be filled with a recognizable material such as a paint contrasting in color to the color of the ring 790, again, for example, white and black, and be read in conjunction with the fine indicia 505 of static housing 500 as an accurate vernier scale. The ring 790 may be attached to the outside of the adjusting nut 602 by dowels 410 about the positions 795.

In FIGS. 4–7 & 52–54 is presented detail of a top cover 810. The cover 810, for example, of aluminum, may have lip 811 and tongue 812. After it is machined, a rulon way strip 813 may be epoxied inside the cover proximate tongue 812. The cover 810 may be attached to the static outer housing 500 by socket head cap screws 400.

Viscometer 2000 may have general symmetry, at least.

Figure 13:
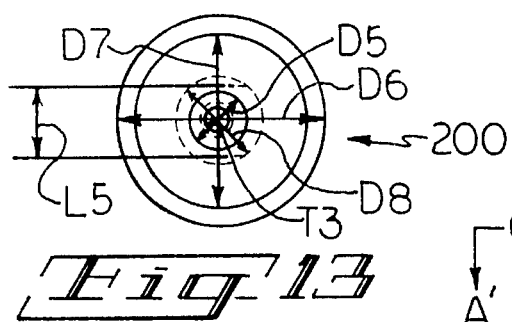
FIG. 13 is a top view of a support rod of the viscometer from FIGS. 3–10.
Figure 14:
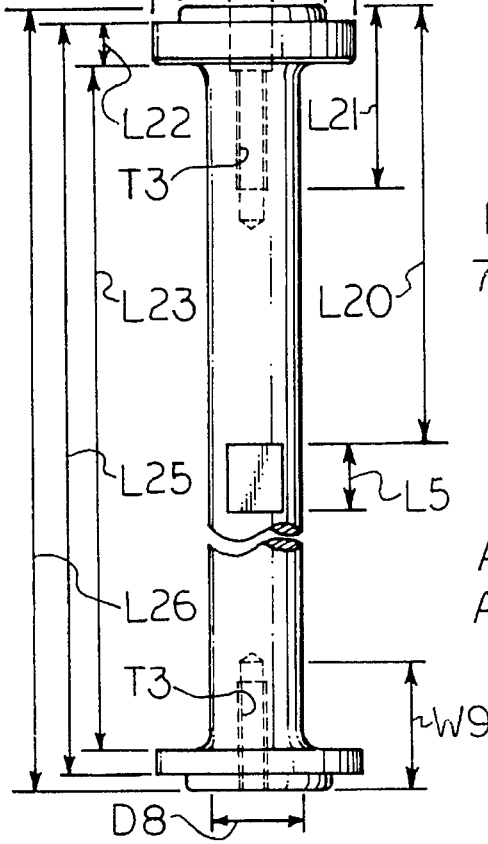
FIG. 14 is a side view of the rod of FIG. 13.
Figure 15:
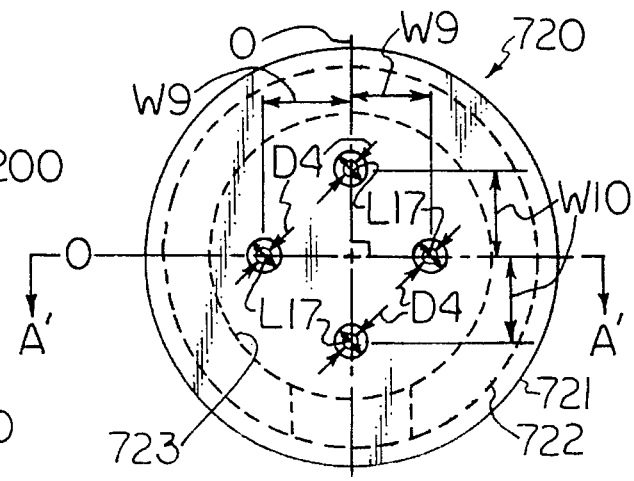
FIG. 15 is a top view of a transducer mount from the viscometer of FIGS. 3–10.
Figure 16:
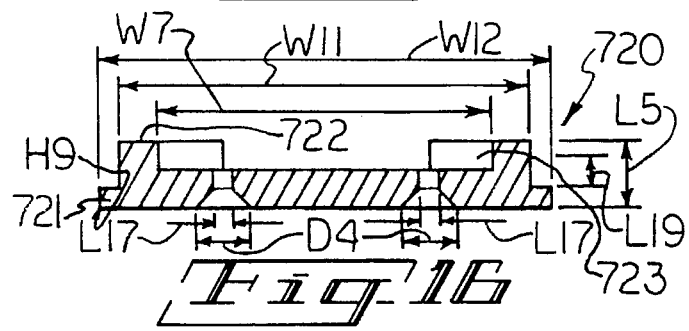
FIG. 16 is a side section of the mount of FIG. 15, taken along A'–A'.
Figure 17:
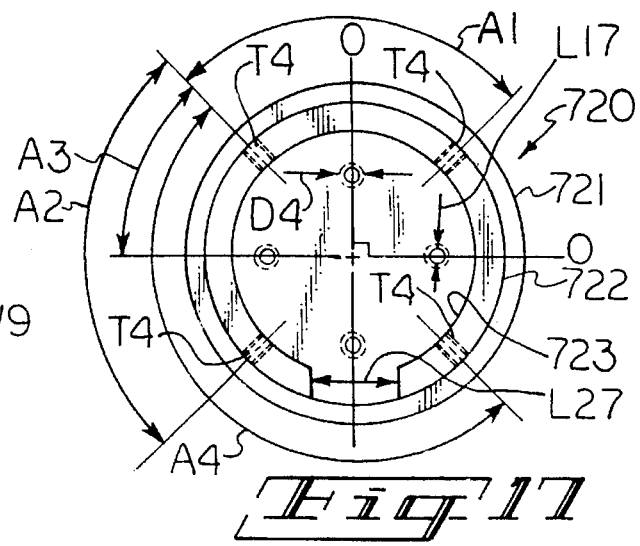
FIG. 17 is a bottom view of the mount of FIGS. 15 & 16.
Figure 23:
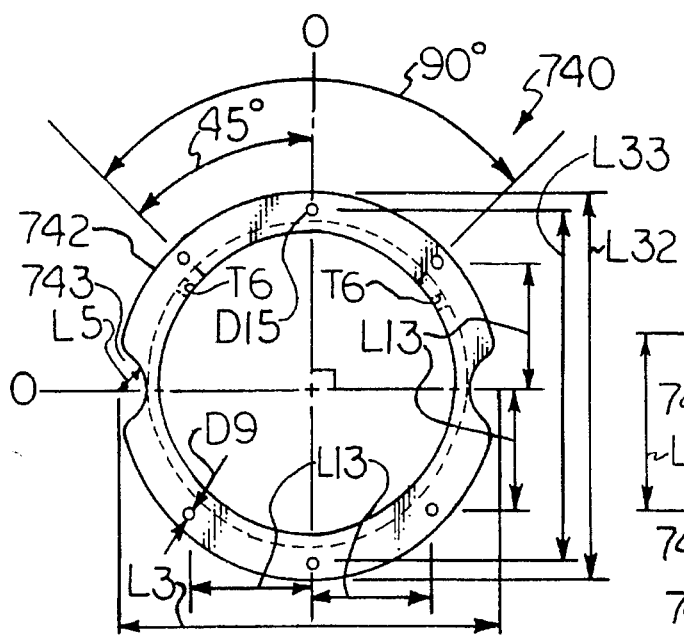
FIG. 23 is a top view of a transducer housing or shell from the viscometer of FIGS. 3–10.
Figure 24:
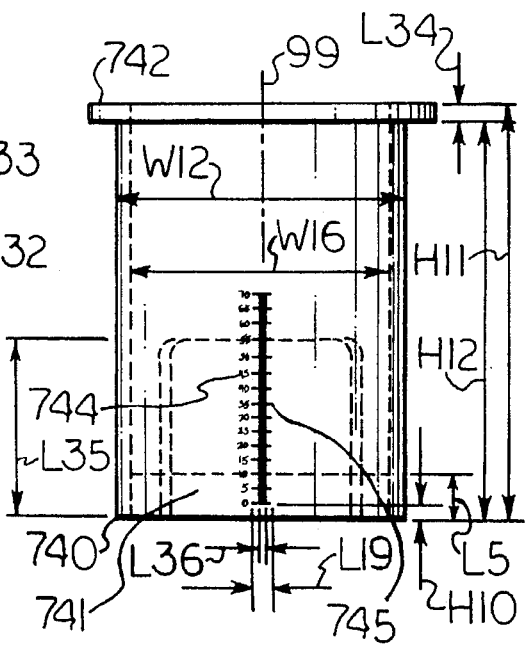
FIG. 24 is a side view of the shell of FIG. 23.
Figure 25:
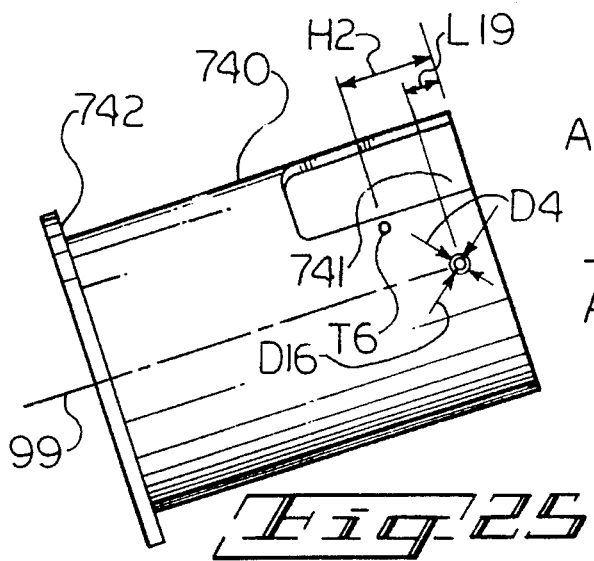
FIG. 25 is another view of the shell of FIG. 23, taken in the direction of the arrow A.
Figure 26:
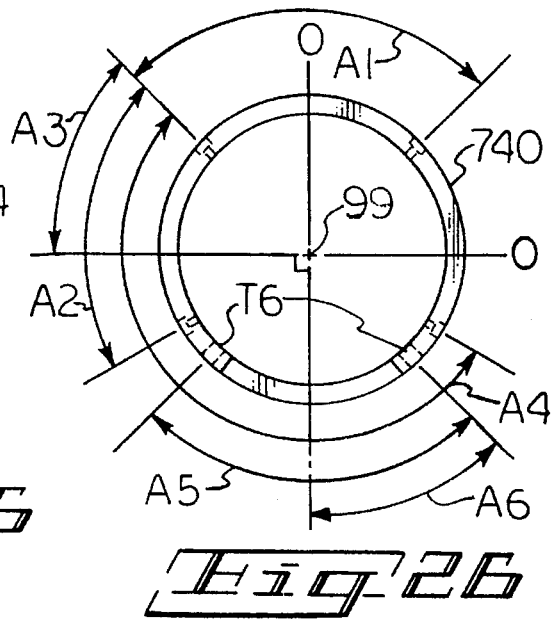
FIG. 26 is a bottom view of the shell of FIGS. 23–25.
Figure 31:
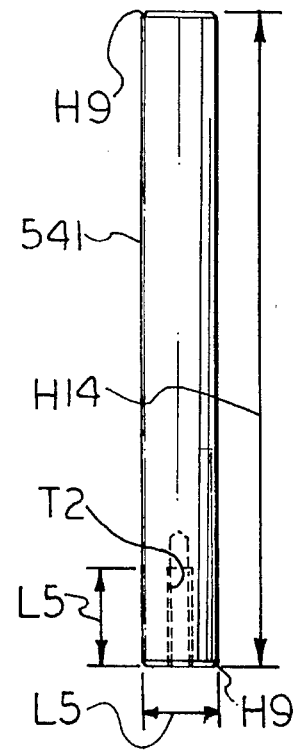
FIG. 31 is a side view of a guide shaft, part of the anti-rotation device of the viscometer from FIGS. 3–10.
Figure 49:
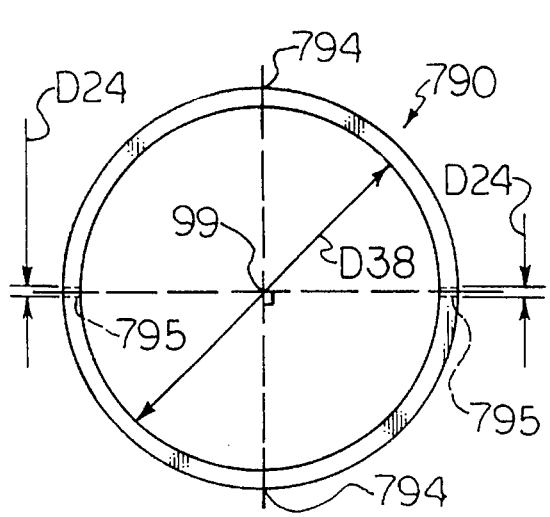
FIG. 49 is a top view of a knurled ring from the viscometer of FIGS. 3–10.
Figure 52:
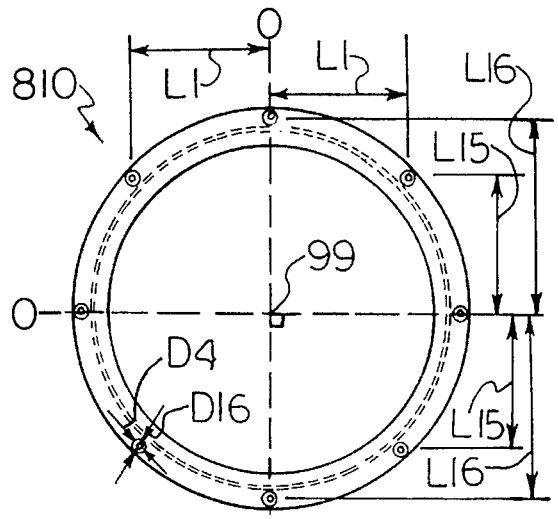
FIG. 52 is a top view of a top cover from the viscometer of FIGS. 3–10.
Figure 50:
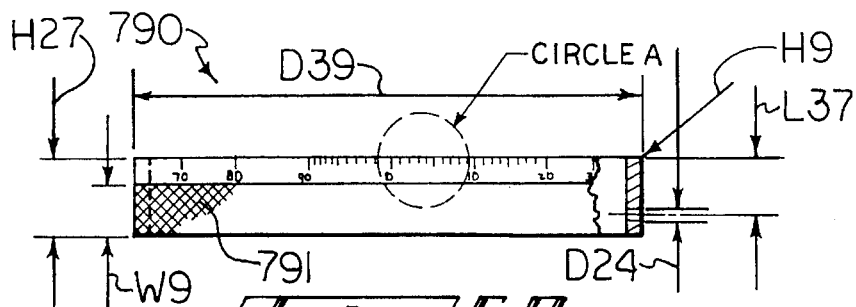
FIG. 50 is a side view of the ring of FIG. 49.
Figure 51:
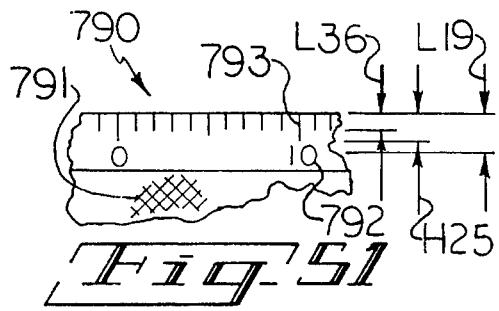
FIG. 51 is an enlarged side view of part of the ring of FIGS. 49 & 50, taken within circle A of FIG. 50.
Figure 53:
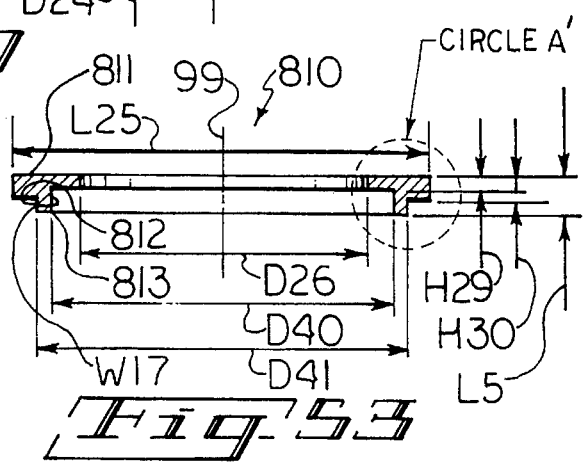
FIG. 53 is a side, cut-away view of the cover of FIG. 52.

In the drawings of viscometer 2000, some dimensions may be measured in relation to an origin line, O. With such a viscometer, some exemplary angles A1 et seq., listed in degrees, and some exemplary dimensions, D1 et seq., H1 et seq., L1 et seq., W1 et seq., listed in inches and which may be converted to centimeters by multiplying by 2.54, serve as being further illustrative of the invention, and the same may be considered to be approximate as may be the angles and dimensions for other features in the drawings, as follows:

A1: 90 (FIGS. 17 & 26).
A2: 70 (FIGS. 17 & 26).
A3: 45 (FIGS. 17 & 26).
A4: 200 (FIGS. 17 & 26).
A5: 102 (FIGS. 26 & 47).
A6: 51 (FIGS. 26 & 47).
D1: 5.25 (FIG. 1); 8.0 (FIG. 4); ≦5 (FIG. 58); 5 (FIG. 59).
D2: 8 (FIGS. 1, 4 & 59).
D3: 1.126 (FIGS. 10 & 11).
D4: 0.31 (FIGS. 10, 11, 15–17, 21, 23, 25, 41, 42 & 52).
D5: 0.41 (FIGS. 10, 11, 29, 30, 43 & 44).
D6: 1.38 (FIGS. 13 & 14).
D7: 1.125 (FIGS. 13 & 14).
D8: 0.63 (FIGS. 13 & 14).
D9: 0.21 (FIGS 18, 19, 23, 29 & 30).
D10: 0.788 (FIG. 18).
D11: 0.14 (FIGS. 18 & 19).
D12: 0.24 (FIGS. 18 & 19).
D13: 2.63 (FIGS. 19 & 20).
D14: 0.236 (FIG. 22 ).
D15: 1.879 (FIG. 23).
D16: 0.17 (FIGS. 23, 25, 26, 29, 30, 33, 39, 41 & 42).
D17: 0.501 (FIGS. 29 & 30).
D18: 8.00 (FIGS. 30 & 34).
D19: 5.625 (FIG. 30).
D20: 4.00 (FIG. 30 ).
D21: 1.126 (FIG. 30).
D22: 7.06 (FIG. 34).
D23: 7.310 (FIG. 36).
D24: 0.1246 (FIGS. 37, 39, 49 & 50).
D25: 5.836 (FIG. 38).
D26: 6.12 (FIGS. 38 & 53).
D27: 4.4990 (FIG. 38).
D28: 6.624 (FIG. 38).
D29: 0.1254 (FIGS. 39 & 41).
D30: 5.88 (FIG. 41).
D31: 6.928 (FIG. 42).
D32: 0.28 (FIGS. 43 & 44 ).
D33: 0.2496 (FIGS. 43 & 44).
D34: 0.1879 (FIG. 45).
D35: 0.627 (FIGS. 45 & 46).
D36: 6.00 (FIG. 46).
D37: 3.81 (FIG. 46).
D38: 6.625 (FIG. 49).
D39: 7.188 (FIG. 50).
D40: 6.968 (FIG. 53).
D41: 7.308 (FIG. 53).
H1: 12 (FIG. 1); 15 (FIG. 59).
H2: 1.250 (FIGS. 4, 5 & 6).
H3: 1.275 (FIGS. 4 & 6).
H4: 5.375 (FIGS. 4 & 6).
H5: 6.875 (FIG. 5).
H6: 6.750 (FIG. 6).
H7: 7.000 (FIG. 6).
H8: 7.250 (FIG. 6).
H9: 0.03×45 degrees (FIGS. 16, 19, 30, 31, 38, 42 & 50) .
H10: 0.13 (FIG. 24).
H11: 5.12 (FIGS. 24 & 30).
H12: 4.398 (FIG. 24).
H13: 0.467 (FIG. 30).
H14: 4.25 (FIG. 31).
H15: 0.125 (FIG. 34).
H16: 1.38 (FIG. 36).
H17: 2.875 (FIG. 36).
H18: 0.06×45 degrees (FIG. 38).
H19: 0.09×45 degrees (FIG. 38).
H20: 3.062 (FIG. 38).
H21: 3.875 (FIG. 38).
H22: 4.500 (FIG. 38).
H23: 4.936 (FIG. 38).
H24: 0.375 (FIGS. 40, 41 & 42).
H25: 0.18 (FIGS. 42 & 51).
H26: 0.97 (FIG. 43).
H27: 1.19 (FIGS. 48 & 50).

Figure 64:
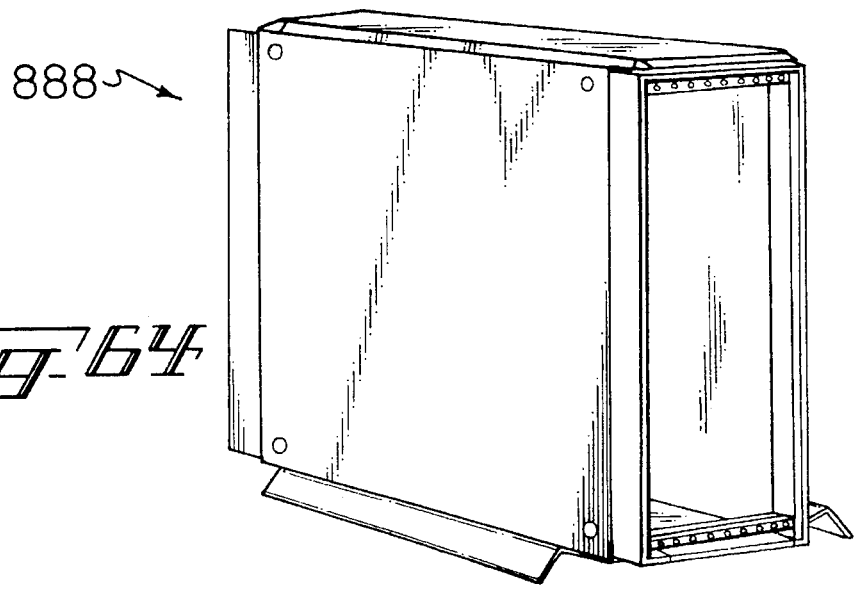
FIG. 64 is a perspective view of a console box housing, which may, in part, accompany a tapered bearing simulator viscometer such as those of the invention and so forth.
Figures 65, 66:
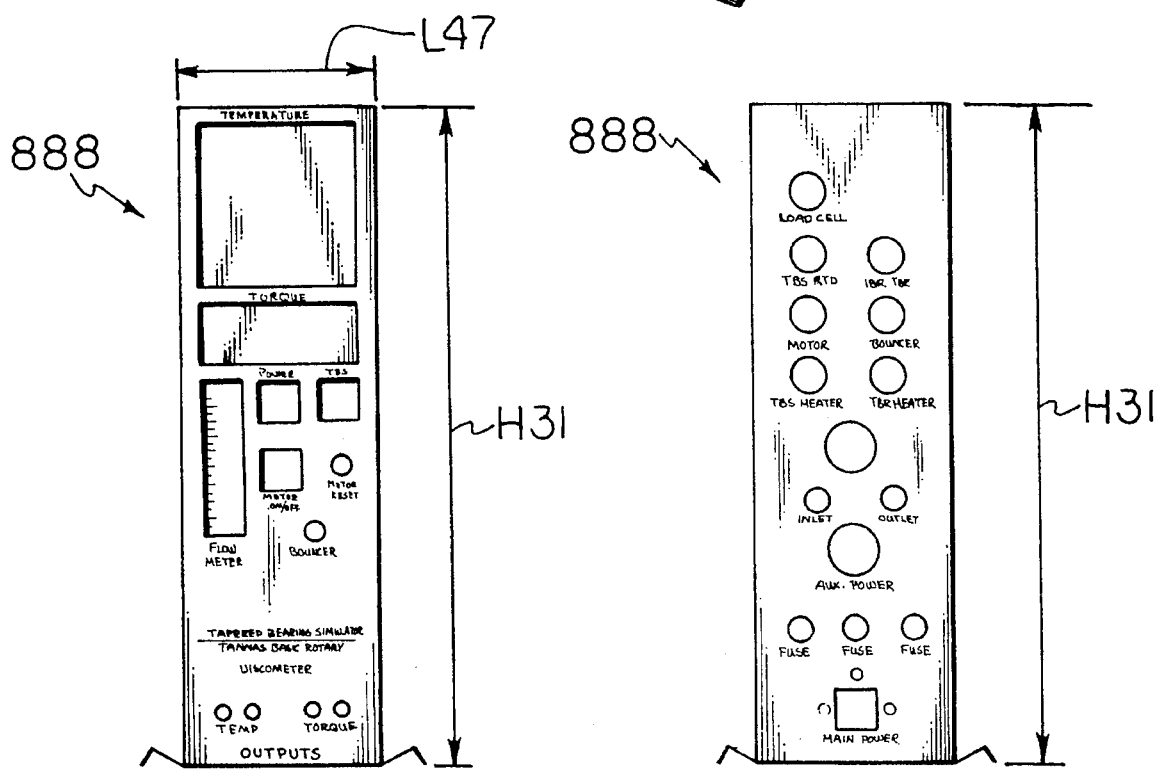
FIG. 65 is a front view of a console box employing the console box housing of FIG. 64.
FIG. 66 is a rear view of the console box of FIG. 65.

H28: 2.38 (FIG. 48).
H29: 0.17 (FIG. 53).
H30: 0.145 (FIG. 53).
H31: 16 (FIGS. 64 & 65).
L1: 3.301 (FIGS. 7, 29, 33, 35 & 52).
L2: 3.217 (FIGS. 7, 37, 39 & 41).
L3: 2.375 (FIGS. 7, 10, 23, 29 & 45).
L4: 2.786 (FIGS. 7, 37, 39 & 41).
L5: 0.500 (FIGS. 9, 16, 20, 21, 23, 24, 31 & 53).
L6: 3.2500 (FIGS. 9, 11 & 29).
L7: 2.298 (FIG. 9).
L8: 1.094 (FIGS. 9 & 11).
L9: 0.625 (FIGS. 9 & 11).
L10: 3.120 (FIGS. 9 & 11).
L11: 1.894 (FIGS. 9 & 11).
L12: 3.301 (FIG. 10).
L13: 1.503 (FIGS. 10, 23 & 45).
L14: 1.062 (FIG. 10).
L15: 1.906 (FIGS. 10, 29, 33 & 52).
L16: 3.812 (FIGS. 10, 29, 33, 35 & 52)
L17: 0.15 (FIGS. 12, 15, 16, 17, 19, 20, 21, 30 & 47)
L18: 0.62 (FIG. 12).
L19: 0.25 (FIGS. 12, 14, 16, 19, 21, 24, 26, 42 & 51)
L20: 3.88 (FIG. 14).
L21: 1.42 (FIG. 14).
L22: 0.42 (FIG. 14).
L23: 7.50 (FIGS. 14, 18 & 19).
L24: 0.12 (FIG. 14).
L25: 8.000 (FIGS. 14 & 53).
L26: 8.25 (FIG. 14).
L27: 1.50 (FIG. 16).
L28: 1.063 (FIGS. 18 & 20).
L29: 1.57 (FIG. 22).
L30: 2.67 (FIG. 22).
L31: 2.50 (FIG. 22).
L32: 4.75 (FIGS. 23 & 39).
L33: 2.1250 (FIGS. 23 & 45).
L34: 0.19 (FIG. 24).
L35: 2.31 (FIGS. 24 & 46).
L36: 0.13 (FIGS. 24, 47, 48 & 51).
L37: 0.812 (FIGS. 29 & 50).
L38: 0.439 (FIG. 30).
L39: 2.25 (FIG. 36).
L40: 5.000 (FIGS. 36 & 45).
L41: 0.38 (FIGS. 36 & 43).
L42: 2.00 (FIG. 36).
L43: 1.609 (FIGS. 37, 39 & 41).
L44: 4.343 (FIG. 38).
L45: 1.88 (FIG. 47).
L46: 0.04 (FIG. 47).
L47: 4.90 (FIG. 64).
W1: 2.298 (FIGS. 4, 5 & 6).
W2: 3.250 (FIGS. 4 & 6).
W3: 1.906 (FIGS. 5 & 7).
W4: 3.182 (FIG. 5).
W5: 2.787 (FIGS. 5 & 29)
W6: 2.412 (FIGS. 5 & 29).
W7: 2.750 (FIGS. 5, 16 & 29).
W8: 3.500 (FIGS. 5, 9, 11 & 29).
W9: 0.750 (FIGS. 6, 14, 15, 18, 36 & 50)
W10: 2.187 (FIG. 11).
W11: 3.449 (FIG. 16).
W12: 3.75 (FIGS. 16 & 24).
W13: 0.649 (FIG. 19).
W14: 0.26 (FIGS. 20 & 21).
W15: 0.787 (FIG. 21).
W16: 3.450 (FIG. 24).
W17: 0.20 (FIG. 53).

Further, in the drawings of viscometer 2000, some exemplary threaded holes, T1 et seq., may serve also in illustration of the invention, and these may be considered as approximate as may other corresponding drawings features, as follows:

T1: 5/16—18 UNC-2B Thread (FIGS. 11 & 12).
T2: #10–24 UNC-2B Thread (FIGS. 11, 12, 29, 30, 31 & 41).
T3: ¼—20 UNC-2B Thread (FIGS. 13, 14, 29, 30 & 36).
T4: #8–32 UNC-2B Thread (FIGS. 17, 35, 36, 37 & 38).
T5: #10–32 UNF-2B Thread (FIGS. 20, 21 & 45).
T6: #4–40 UNC-2B Thread (FIGS. 23, 25 & 26).

In operating an embodiment such as illustrated, adjusting nut 602 is rotated to raise and lower adjusting screw 550 and platform 60 with motor 56, shaft 51 and drum 50 in bore 25. The operator can read out the consequent height, which corresponds to the aforementioned thin measuring gap, through use of the above-noted general and vernier indicia.

Other methods of height adjustment may be employed. For instance, digital height instrumentation 555, well-known in the art, can be used (FIG. 55).

At a suitable height, the drum 50 is turned in bore 25 having a standard reference or test fluid therein, and drag on the motor 56 and drum 50 corresponding to the viscosity of the fluid at the temperature of interest is measured by the transducer 86. Data may be input into computer assembly 777 (FIG. 55) or computer console 888 (FIGS. 64–66) for processing, readout, calibration, and test runs.

Accordingly, the viscometer of the present invention is operated similarly to the viscometer of the Selby patent.

Alternatively, a gear-driving motor may be employed to turn the adjusting nut 602. Since it is known to inject a number of sample fluids automatically into test cell 23, by employing an automated gear-driving motor in place of hand drive 697 (FIG. 55), and suitable height-readout and/or data-processing equipment, the viscometer of the invention may be fully automated.

Accordingly, as illustrated above and in the drawings, it can be seen that the linear translocating or elevator mechanism part externally bounds the axis of rotation of the motor, drive shaft, and rotor, and that this is an important feature of the present invention. This mechanism can include the rotating shell or nut, platform periphery, and anti-rotation device. The static housing may protect the workings of this mechanism, and it may include or provide access to height-indicating parts of the mechanism.

Other features are seen within the drawings and writings.

The principles of the viscometer of the invention as illustrated in detail herein can be applied to a dynamometer as well. More particularly, the dynamometer is generally a rotational dynamometer, for measuring force or energy such as the resistive force of friction between solids in contact, moving fluids such as gases and liquids in contact with (a) moving surface(s) and the resistive force of magnetic and electro-magnetic fields.

CONCLUSION

The present invention is thus provided. Numerous modifications can be effected within its spirit, the literal claim scope of which is particularly pointed out as follows.

We claim:

1. A stacked component force measuring device comprising an cooperating element to provide a resistive force for measurement, wherein said element includes a component or material under test; a rotor in communication with the element, the rotor having a drive shaft extending axially from it; a motor housing, which can rotate in response to torque or drag generated on the rotor from the element, including a motor which drives the shaft and rotor around an axis of rotation; a means for sensing force exerted on the motor housing with respect to the element during rotation of the rotor, which means for sensing force is fixable to said motor housing, and which means for sensing force is connectable to a platform that is adjustable in a direction of the axis of rotation by a linear translocating mechanism, which generally, externally bounds the axis of rotation of the motor, drive shaft, and rotor where said device has said rotor and said drive shaft mounted in a vertically-stacked manner, and having said motor, said motor housing, said platform and said means for sensing force mounted in a vertically-stacked, spatially-compacted manner.

2. The device of claim 1, wherein the linear translocating mechanism comprises a threaded arrangement with an anti-rotation device wherein a first set of threads resides with the platform, which is restrained from rotating by the anti-rotation device but allowed to be moved in the direction of the axis of rotation, and a second set of threads for mating with said first set of threads resides with at least one rotatable member separate from but threadedly engagable with said first set of threads of the platform.

3. The device of claim 1, which is a dynamometer.

4. The device of claim 2, which is a dynamometer.

5. The device of claim 3, which is a viscometer.

6. The device of claim 4, which is a viscometer.

7. The device of claim 2, wherein said first set of threads which resides with the platform is disposed on the platform to form a male set of threads about an outer boundary of the platform, and said second set of threads which resides with said at least one rotatable member is disposed on said at least one rotatable member to form a corresponding female set of threads.

8. The device of claim 7, which has a vernier scale in conjunction with a rotatable nut part of the linear translocating mechanism to indicate distance moved by the platform in the direction of the axis of rotation of the linear translocating mechanism.

9. A stacked component tapered bearing simulator device comprising a stator block having a sample receiving bore; a rotor with a shape complementary to the stator block bore extending axially into the sample receiving bore to define therebetween a thin measuring gap, which thin measuring gap receives a sample of a test fluid for data collection with said simulator device, the rotor having a drive shaft extending axially upward from it; a motor housing, which can rotate in response to torque or drag generated on the rotor from a test sample present in the thin measuring gap, including a motor which drives the shaft and rotor around an axis of rotation; a means for sensing the torque generated on the rotor by the test sample in the thin measuring gap and communicated to said motor housing, which means for sensing the torque is fixable to said motor housing, and which means for sensing the torque is connectable to a platform that is vertically adjustable by an elevator mechanism, which elevator mechanism generally, externally bounds the axis of rotation of the motor, drive shaft, and rotor where said device has said rotor, said stator block and said drive shaft mounted in a vertically-stacked manner, and having said motor, said motor housing, said platform, said elevator mechanism and said means for sensing torque mounted in a vertically-stacked, spatially-compacted manner.

10. The device of claim 9, wherein the elevator mechanism comprises a threaded arrangement with an anti-rotation device wherein a first set of threads resides with the platform, which is restrained from rotating by the anti-rotation device but allowed to be moved vertically, and a second set of threads for mating with said first set of threads resides with at least one rotatable member separate from but threadedly engagable with said first set of threads of the platform.

11. The device of claim 10, wherein said first set of threads which resides with the platform is a male set of threads about an outer boundary of the platform, and said second set of threads which resides with said at least one rotatable member is a corresponding female set of threads.

12. The viscometer of claim 11, which has a vernier scale in conjunction with a rotatable nut part of the elevator mechanism to indicate height of the elevator mechanism.

13. A stacked component tapered bearing simulator viscometer comprising a stator block having a sample receiving bore; a rotor with a shape complementary to the stator block bore extending axially into the sample receiving bore to define therebetween a thin measuring gap, which thin measuring gap receives a sample of a test fluid for data collection for measurement of viscosity of the test fluid with said simulator device, the rotor having a drive shaft extending axially upward from it; a motor housing, which can rotate in response to torque or drag generated on the rotor from a test sample present in the thin measuring gap, including a motor which drives the shaft and rotor around an axis of rotation; a means for sensing the torque generated on the rotor by the test sample in the thin measuring gap and communicated to said motor housing, which means for sensing the torque is fixable to said motor housing, and which means for sensing the torque is connectable to a platform that is vertically adjustable by an elevator mechanism, which elevator mechanism generally, externally bounds the axis of rotation of the motor, drive shaft, and rotor, and which elevator mechanism comprises a threaded arrangement with an anti-rotation device wherein a first set of threads resides with the platform, which is restrained from rotating by the anti-rotation device but allowed to be moved vertically, and a second set of threads for mating with said first set of threads resides with at least one rotatable member separate from but threadedly engagable with said first set of threads of the platform.

14. The viscometer of claim 13, wherein said second set of threads for mating with said first set of threads is provided on several upraised portions of said at least one rotatable member and wherein said first set of threads which resides with the platform is a male set of threads about an outer boundary of the platform, and said second set of threads which resides with said at least one rotatable member is a corresponding female set of threads.

15. The viscometer of claim 13, wherein said first set of threads which resides with the platform is a male set of threads about an outer boundary of the platform, and said second set of threads which resides with said at least one rotatable member is a corresponding female set of threads.

16. The viscometer of claim 15, which has a vernier scale in conjunction with a rotatable nut part of the elevator mechanism to indicate height of the elevator mechanism.

17. The viscometer of claim 13, wherein the motor is a DC motor.

18. The viscometer of claim 17, wherein low-interference motor and load cell wiring connections are employed so as to ameliorate physical interference in measurement of the torque as can be otherwise caused by dangling wiring.

19. The viscometer of claim 13, wherein the means for measuring torque includes an in-line load cell.

20. The viscometer of claim 18, wherein the means for measuring torque includes an in-line transducer.

* * * * *